United States Patent
Yim et al.

(10) Patent No.: US 10,993,434 B2
(45) Date of Patent: May 4, 2021

(54) **CRYOPROTECTIVE AGENT CONTAINING EXOPOLYSACCHARIDE FROM *PSEUDOALTEROMONAS* SP. CY01**

(71) Applicant: KOREA INSTITUTE OF OCEAN SCIENCE AND TECHNOLOGY, Gyeonggi-do (KR)

(72) Inventors: Joung Han Yim, Gyeonggi-do (KR); Il-Chan Kim, Gyeonggi-do (KR); Se Jong Han, Gyeonggi-do (KR); Ui Joung Youn, Incheon (KR); Hong Kum Lee, Gyeonggi-do (KR); Sung Jin Kim, Incheon (KR); Pil-Sung Kang, Jeollabuk-do (KR); Jung Eun Kim, Gangwon-do (KR); Tai Kyoung Kim, Incheon (KR); Ha Ju Park, Gyeonggi-do (KR); Jin Haeng Song, Incheon (KR); Min Ju Kim, Incheon (KR); Ju Mi Hong, Daejeon (KR); Dong-Gyu Jo, Gyeonggi-do (KR)

(73) Assignee: Korea Institute of Ocean Science and Technology, Gyeonggi-Do (KR)

( * ) Notice: Subject to any disclaimer, the term of this patent is extended or adjusted under 35 U.S.C. 154(b) by 0 days.

(21) Appl. No.: 15/836,138

(22) Filed: Dec. 8, 2017

(65) Prior Publication Data
US 2018/0325101 A1     Nov. 15, 2018

(30) Foreign Application Priority Data
May 11, 2017   (KR) .................. 10-2017-0058701

(51) Int. Cl.
*A01N 1/02*   (2006.01)
*C12P 19/04*  (2006.01)
*C12N 1/20*   (2006.01)
*C12R 1/01*   (2006.01)
*C08B 37/00*  (2006.01)

(52) U.S. Cl.
CPC .......... *A01N 1/0221* (2013.01); *C08B 37/006* (2013.01); *C12N 1/20* (2013.01); *C12P 19/04* (2013.01); *C12R 1/01* (2013.01)

(58) Field of Classification Search
CPC .. A01N 1/10221; A01N 1/021; A01N 1/0221; C12P 19/04; C08B 37/00
See application file for complete search history.

(56) References Cited

U.S. PATENT DOCUMENTS 5,071,741 A * 12/1991 Brockbank .............. A01N 1/02
                                                    128/898

FOREIGN PATENT DOCUMENTS

KR     20040071964 A  *  8/2004

OTHER PUBLICATIONS

Cohen et al. Extracellular Polysaccharides of Azobacter Vinelandii; Journal of Bacteriology, vol. 88, No. 2, pp. 329-338. (Year: 1964).*
Tallon et al. Isolation and Characterization of Two Exopolysaccharides Produced by Lactobacillus Plantarum EP56; Research and Microbiology, vol. 154, pp. 705-712. (Year: 2003).*
Saravanan et al. Preliminary Characterization of Exopolysaccharides Produced by a Marine Biofilm-Forming Bacterium Pseudoateromonas Ruthenica (SBT 033); Letters in Applied Microbiology, vol. 46, pp. 1-6. (Year: 2008).*
Holmstrum et al. Marine Pseudoalteromonas Species Are Associated With Higher Organisms and Produce Biologically Active Extracellular Agents; FEMS Microbiology Ecology, vol. 30, pp. 285-293. (Year: 1999).*
Carol Mancuso Nichols, Sandrine Garon Lardière, John P. Bowman, Peter D. Nichols, John A. E. Gibson, and Jean Guèznnec, "Chemical Characterization of Exopolysaccharides from Antarctic Marine Bacteria," Microbial Ecology, vol. 49, 578-589 (2005).
KIPO Notification for Reason for Refusal in KR Application No. 10-2017-0058701, dated Sep. 6, 2017.
Response by Applicant to KIPO Notification for Reason for Refusal in KR Application No. 10-2017-0058701, dated Nov. 3, 2017.
KIPO Notice for Granting Patent in KR Application No. 10-2017-0058701, dated Nov. 24, 2017.
Deller, R. C., et al., "Synthetic polymers enable non-vitreous cellular cryopreservation by reducing ice crystal growth during thawing", "Nature Communications", Feb. 3, 2014, pp. 1-7; DOI: 10.1038/ncomms4244, vol. 5, No. 3244.
Horn, E.-P., et al., "Transfusion of Autologous, Hydroxyethyl Starch-Cryopreserved Red Blood Cells", "Applied and Environmental Microbiology", Jun. 18, 1997, pp. 739-745, vol. 85.
Kim, S. J., et al., "Cryoprotective Properties of Exopolysaccharide (P-21653) Produced by the Antarctic Bacterium, Pseudoalteromonas arctica KOPRI 21653", "The Journal of Microbiology", Dec. 2007, pp. 510-514, vol. 45, No. 6.
Liu, S.-B., et al., "Structure and Ecological Roles of a Novel Exopolysaccharide from the Arctic Sea Ice Bacterium *Pseudoalteromonas* sp. Strain SM20310", "Applied and Environmental Microbiology", Jan. 2013, pp. 224-230, vol. 79, No. 1.
Scott, K. L., et al., "Biopreservation of Red Blood Cells: Past, Present, and Future", "Transfusion Medicine Reviews", Apr. 2005, pp. 127-142, vol. 19, No. 2.

(Continued)

*Primary Examiner* — Susan M Hanley
*Assistant Examiner* — Paul C Martin
(74) *Attorney, Agent, or Firm* — Troutman Pepper Hamilton Sanders LLP; Ryan A. Schneider; Chris N. Davis

(57) ABSTRACT

The present invention relates to an exopolysaccharide derived from *Pseudoalteromonas* sp. strain CY01 (KCTC 12867BP) which is a novel strain living in the polar regions, and to a composition for cryoprotection of cells, which contains the exopolysaccharide. The exopolysaccharide of the present invention has an excellent ability to cryoprotect cells, and shows no cytotoxicity. Thus, the inventive exopolysaccharide can substitute for conventional cryoprotective agents that show cytotoxicity when used at high concentrations.

2 Claims, 17 Drawing Sheets
(13 of 17 Drawing Sheet(s) Filed in Color)

(56) References Cited

OTHER PUBLICATIONS

Stolzing, A., et al., "Hydroxyethylstarch in cryopreservation Mechanisms, benefits and problems", "Transfusion and Apheresis Science", Jan. 23, 2012, pp. 137-147, vol. 46.

* cited by examiner

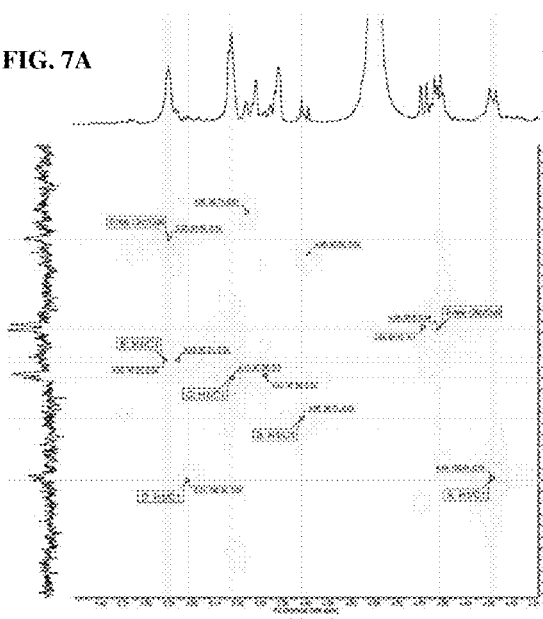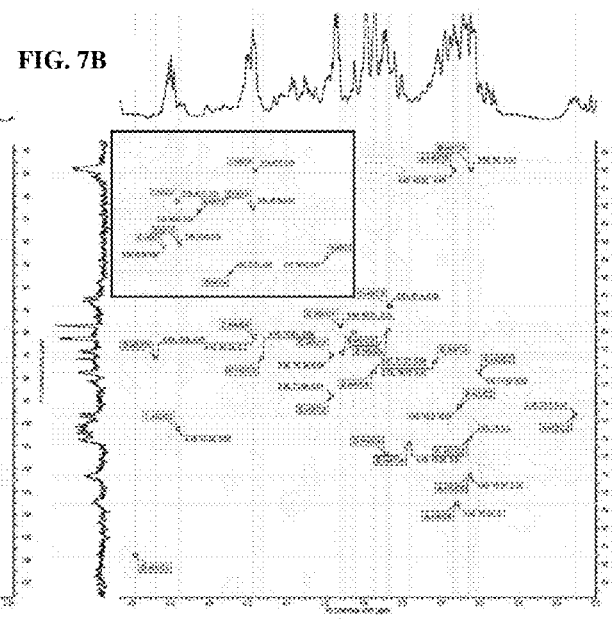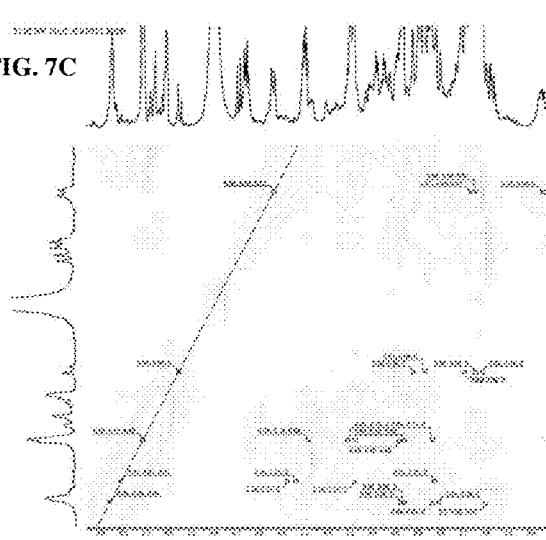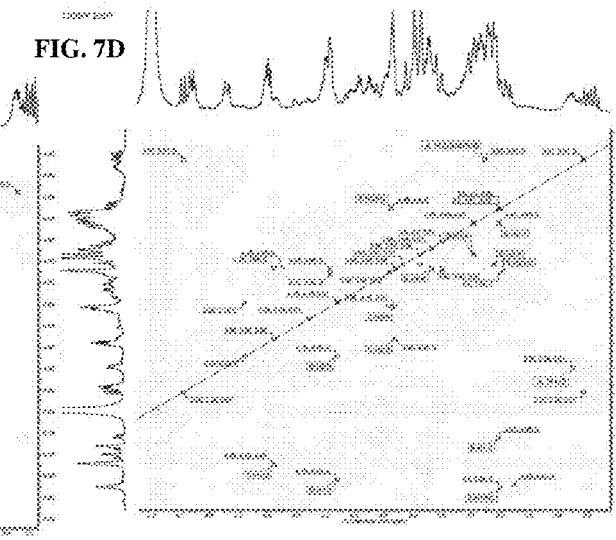

CRYOPROTECTIVE AGENT CONTAINING EXOPOLYSACCHARIDE FROM *PSEUDOALTEROMONAS* SP. CY01

CROSS-REFERENCE TO RELATED APPLICATIONS

This application claims priority under 35 U.S.C. § 119 of Korean Patent Application No. 10-2017-0058701 filed May 11, 2017. The disclosure of such Korean priority patent application is hereby incorporated herein by reference in its entirety, for all purposes.

TECHNICAL FIELD

The present invention relates to an exopolysaccharide derived from *Pseudoalteromonas* sp. strain CY01 that is a novel strain living in the polar regions, and more particularly to an exopolysaccharide derived from *Pseudoalteromonas* sp. strain CY01 and to a composition for cryoprotecting cells, which contains the exopolysaccharide.

BACKGROUND ART

Many kinds of bacteria that live in the marine environment secrete viscous extracellular hydrocarbon polymers known as exopolysaccharides (EPSs). Most EPSs produced by marine bacteria are heteropolysaccharides consisting of 3 or 4 different monosaccharides that may be pentoses, hexoses, amino sugars or uronic acids and are arranged in groups of 10 or more to form repeating units. EPSs function to protect microorganisms from cold environments, and EPSs secreted by bacteria in polar cold environments have new structures and cryoprotective abilities in many cases.

It was found that the EPSs secreted from *Pseudoalteromonas* sp. SM20310 (Arctic bacteria) and *Pseudoalteromonas arctica* KOPRI 21653 (Antarctic bacteria) enhance the viability of *E. coli* (bacteria in non-polar regions) against freeze-thaw cycles. Thus, the usability of EPSs from these bacteria as cryoprotective agents (CPAs) has been proposed (Liu, S. B. et al. *Applied and Environmental Microbiology*, 79:224, 2013; Kim, S J & Yim, J. H., *J. Microbiology*, 45:510, 2007).

The formation and growth of ice causes physical damage at cellular level, and also reduces the volume of water in solution to cause osmotic shock due to an increased concentration of extracellular solution. This becomes a problem when biological substances are stored at temperatures lower than the freezing temperatures.

As regenerative medicine and organ transplantation are growing rapidly, the need for cryopreservation of donor cells, tissues, organs and red blood cells (RBCs) is increasing. Generally, packed blood is stored in an additive solution such as ADSOL at 4° C. for 42 days without cryopreservation, and undergoes a high rate of hemolysis. This problem can be overcome by using glycerol as a cryoprotective agent. However, high ability to recover red blood cells can be retained, only when a high concentration (40% w/v or higher) of glycerol is added to the cells and the cells are cooled at a very slow cooling rate of 1° C./min and stored at −80° C.

However, cytotoxicity of glycerol is removed only when glycerol is diluted to 1% or less by washing after thawing. To overcome this disadvantage of glycerol, there have been continued attempts to use other cryoprotective agents including low molecular sugars such as trehalose, sucrose, glucose, raffinose, maltose and the like. However, this method may have an impact on the final freezing of red blood cells due to problems such as osmotic pressure or oxidation. In order to simplify a complex washing process after thawing, there have been attempts to use non-penetrating additives, such as HES (hydroxyethyl starch), polyvinyl pyrrolidone and dextran, in place of glycerol (Scott, K. L. et al., *Transfus. Med. Rev.*, 19:127, 2005; Stolzing, A. et al., *Transfusion Apheresis Sci.*, 46:137, 2012; E. P. Horn et al., *Anesth. Analg.*, 85:739, 1997). Such polymers do not penetrate the cell membrane and are present only outside the cell membrane, and thus do not require a complex washing process during thawing after freezing of red blood cells. However, for cryopreservation of red blood cells, a high concentration (20% w/v or higher) of HES solution is required, and this high concentration results in high viscosity, making it difficult to handle a freezing process.

Accordingly, the present inventors have made extensive efforts to find a cryoprotective agent which is non-penetrating, is less cytotoxic, and has an excellent cryoprotective effect. As a result, the present inventors have found that when an exopolysaccharide (EPS) produced by *Pseudoalteromonas* sp. strain CY 01 (KCTC 12867BP) that is a novel strain living in the Antarctic Ocean is added during cryopreservation of red blood cells, it exhibits an excellent cryoprotective effect at a relatively low concentration compared to other cryoprotective agents (CPAs) and shows no cytotoxicity, thereby completing the present invention.

DISCLOSURE OF INVENTION

Technical Problem

It is an object of the present invention to provide an exopolysaccharide (p-CY01) derived from *Pseudoalteromonas* sp. strain CY01 (KCTC 12867BP) having the ability to cryoprotect cells, and a method for producing the same.

Another object of the present invention to provide an exopolysaccharide having a molecular weight of $1.0 \times 10^5$ to $4.3 \times 10^5$ Da, which is obtained by hydrolysis of a strain CY01-derived exopolysaccharide, and a method for producing the same.

Still another object of the present invention to provide a composition for cryoprotecting cells which contains the above-described exopolysaccharide (p-CY01 or p-CY01_LM).

Yet another object of the present invention to provide a method for cryopreserving cells using the above-described exopolysaccharide (p-CY01 or p-CY01_LM).

A further object of the present invention to provide a *Pseudoalteromonas* sp. strain CY01 (KCTC 12867BP) which lives in the polar regions and has the ability to produce an exopolysaccharide.

Technical Solution

To achieve the above object, the present invention provides an exopolysaccharide (p-CY01) which is produced by *Pseudoalteromonas* sp. strain CY01 (KCTC 12867BP) and is composed of glucose and galactose.

The present invention also provides an exopolysaccharide (p-CY01_LM) having a molecular weight of $1.0 \times 10^5$ to $4.3 \times 10^5$ Da, which is obtained by hydrolysis of the above-described exopolysaccharide (p-CY01).

The present invention also provides a composition for cryoprotecting cells which contains the above-described exopolysaccharide (p-CY01 or p-CY01_LM).

The present invention also provides a method for producing the exopolysaccharide (p-CY01) which is produced by *Pseudoalteromonas* sp. strain CY01 (KCTC 12867BP) and is composed of glucose and galactose, the method comprising the steps of: (a) culturing *Pseudoalteromonas* sp. strain CY01 (KCTC 12867BP) to produce the exopolysaccharide (p-CY01); and (b) recovering the produced exopolysaccharide (p-CY01).

The present invention also provides a method for producing the exopolysaccharide (p-CY01_LM) having a molecular weight of $1.0 \times 10^5$ to $4.3 \times 10^5$ Da, the method comprising a step of hydrolysis of the exopolysaccharide (p-CY01) which is produced by *Pseudoalteromonas* sp. strain CY01 (KCTC 12867BP) and which is composed of glucose and galactose.

The present invention also provides a method for cryopreserving cells using the above-described exopolysaccharide (p-CY01 or p-CY01_LM).

The present invention also provides a *Pseudoalteromonas* sp. strain CY01 (KCTC 12867BP) which has the ability to produce a mucous exopolysaccharide.

Advantageous Effects

The exopolysaccharide of the present invention has an excellent ability to cryoprotect cells during cryopreservation, and shows no cytotoxicity. Thus, the inventive exopolysaccharide can substitute for conventional cryoprotective agents that show cytotoxicity and require a complicated thawing process when used at high concentrations for cryopreservation of red blood cells. Accordingly, the exopolysaccharide of the present invention is effective for long-term cryopreservation of blood.

BRIEF DESCRIPTION OF THE DRAWINGS

The patent or application file contains at least one drawing executed in color. Copies of this patent or patent application publication with color drawing(s) will be provided by the Office upon request and payment of the applicable fee.

In FIG. 1, the white bars indicate produced EPS, and the black bars indicate the cryoprotective effect (%) of EPS against *E. coli*. Standard deviation (±SD) was obtained three independent experiments.

FIG. 3A shows the results of anion chromatography, and FIG. 3B shows the results of gel filtration chromatography.

FIGS. 7A and 7B show the 2D-HSQC spectrum of p-CY01_LM obtained by low molecularization and shows the results of proton-carbon correlation experiments, and FIGS. 7C, 7D, 7E and 7F show 2D-TOCSY, 2D-COSY, 2D-HMBC and 2D-NMR (600 MHz) spectra.

In FIGS. 10A and 10D, the black bars indicate the hemolysis (%) of red blood cells thawed after cryopreservation in 2.5% p-CY01_LM solution, and the white bars indicate the hemolysis (%) of red blood cells thawed after cryopreservation in PBS solution.

In FIG. 12A, ADSOL indicates ADSOL solution; "G+D" indicates 1% (w/v) glycerol and DMSO; "p-CY01_LM" indicates 2.5% (w/v) p-CY01_LM solution; and "G+D+p-CY01_LM" indicates a solution containing 1% (w/v) glycerol, 1% (w/v) DMSO and 2.5% (w/v) p-CY01_LM. * indicates a solution of each component in ADSOL.

FIG. 13A shows DSC analysis results for a solution containing 1% glycerol and 1% DMSO, which is a negative control; FIG. 13B shows DSC analysis results for a solution containing 1% glycerol, 1% DMSO and 0.5% p-CY01_LM; and FIG. 13C shows DSC analysis results for a solution containing 1% glycerol, 1% DMSO and 2.5% p-CY01_LM.

Figure 16A:
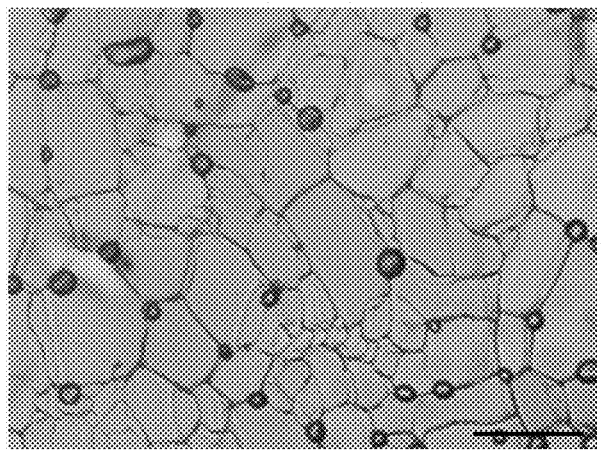
Figure 16B:
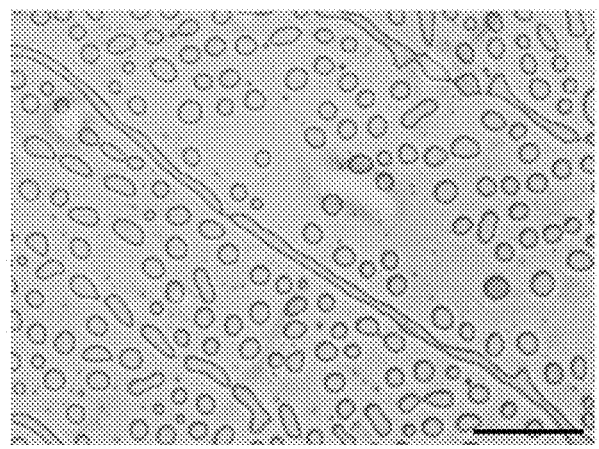
Figure 16C:
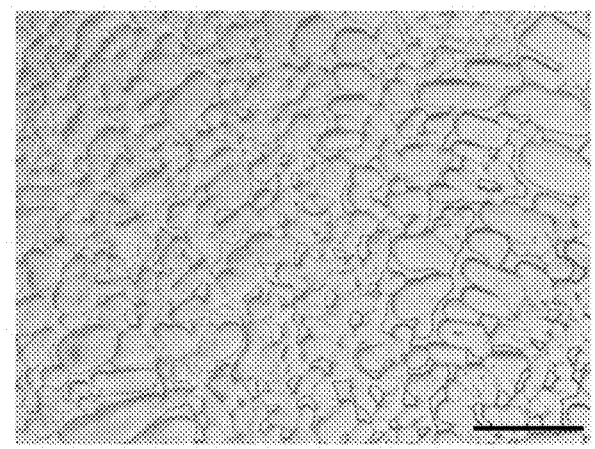

FIGS. 16A through 16C show the results of observing the ice recrystallization inhibition (IRI) activity of p-CY01_LM. Specifically, FIG. 16A shows the results for PBS; FIG. 16B shows the results for p-CY01_LM solution; and FIG. 16C shows the results for an ADSOL solution containing 1% glycerol, DMSO and 2.5% HES. The scale represents 100 μm.

BEST MODE FOR CARRYING OUT THE INVENTION

In the present invention, novel *Pseudoalteromonas* sp. strain CY01 that produces an exopolysaccharide was isolated from Antarctic seawater samples. It was found that the exopolysaccharide produced by the CY01 strain had a high cryoprotective effect against *E. coli* during initial screening. Based on this result, whether the exopolysaccharide produced by the CY01 strain would be usable as a cryoprotective agent during cryopreservation of cells was examined. To have physical properties suitable for use in cryopreservation, the exopolysaccharide from CY01 was partially decomposed by acid to form a low-molecular exopolysaccharide, and the low-molecular exopolysaccharide was added during cryopreservation of red blood cells. As a result, it was shown that the low-molecular exopolysaccharide exhibited high anti-freezing ability and had no cytotoxicity.

Therefore, in one aspect, the present invention is directed to an exopolysaccharide which is produced by *Pseudoalteromonas* sp. strain CY01 (KCTC 12867BP) and which is composed of glucose and galactose.

In the present invention, among 2,980 strains isolated from Antarctic seawater samples, 73 strains that produce mucous exopolysaccharides were isolated, and 10 strains having an excellent ability to produce exopolysaccharides were selected therefrom. *E. coli* cells were subjected to freezing-thawing cycles in 0.2% (w/w) crude exopolysaccharide solution obtained from each strain, and the survival ratio of the *E. coli* cells was measured. As a result, the crude exopolysaccharide produced by the CY01 strain among the 10 strains showed the highest cryoprotective effect.

In an example of the present invention, the survival ratio of *E. coli* cells in a solution containing 0.2% crude exopolysaccharide derived from the CY01 strain was 88.16±2.92%, and the survival ratios of *E. coli* cells in solutions containing 0.2% crude exopolysaccharides derived from other strains were 42.01±1.93% to 67.28±4.32%.

In the present invention, molar ratio of the glucose and the galactose in the exopolysaccharide from CY01 may be approximately 3.4:1.

In the present invention, glycosyl linkage analysis and NMR analysis of the exopolysaccharide from CY01 indicate that the exopolysaccharide has a repeating structure consisting mainly of 4-linked glucopyranose and 6-linked galactopyranose, and these components may be components forming the main chain.

In another aspect, the present invention is directed to an exopolysaccharide having a molecular weight of $1.0 \times 10^5$ to $4.3 \times 10^5$ Da, which is obtained by hydrolysis of the above-described exopolysaccharide.

In the present invention, acid decomposition was performed in order to increase the solubility of the exopolysaccharide and to reduce the high viscosity of the exopolysaccharide, which causes difficulty in handling and washing during the use of the exopolysaccharide as a cryoprotective agent.

In an example of the present invention, the CY01-derived exopolysaccharide (p-CY01) was heated together with 0.1 M of TFA at 121° C. for 1 hour to obtain acid-decomposed p-CY01 (p-CY01_LM). As a result, the average molecular weight of p-CY01 was about $1.1 \times 10^7$ Da, whereas the molecular weight of p-CY01_LM partially decomposed by acid was $1.0 \times 10^5$ to $4.3 \times 10^5$ Da. A decrease in viscosity and an increase in solubility of the exopolysaccharide depending on changes in the rheological properties of the low-molecular p-CY01_LM solution were confirmed.

In still another aspect, the present invention is directed to a composition for cryoprotecting cells which contains the exopolysaccharide.

Figure 7E:
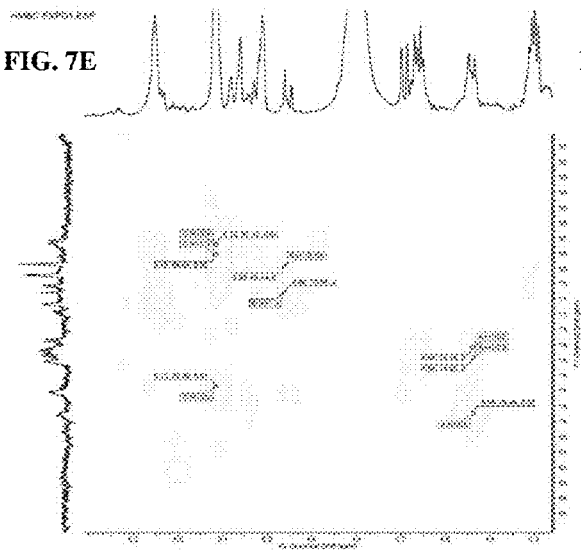
Figure 7F:
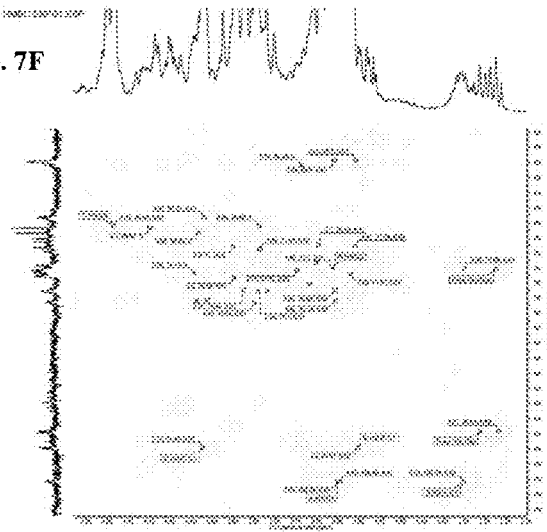

In an example of the present invention, a red blood cell sample containing p-CY01_LM and a cryoprotective agent was frozen without controlling cooling rate (cooled immediately to −80° C.) and preserved at −80° C. The red blood cell sample was rapidly thawed in a water bath at 40° C. After thawing, the function of p-CY01_LM as a cryoprotective agent was analyzed by a red blood cell hemolysis assay and optical microscopic analysis. The hemolysis (%) decreased as the concentration of p-CY01_LM increased. At a p-CY01_LM concentration of 2.5% to 4.0%, a percent hemolysis of 9.08±0.37% to 5.64±0.96% appeared, and the use of 3.5% p-CY01_LM showed the lowest hemolysis (5.40%). In other words, it was shown that, at a p-CY01_LM concentration of 2.5% to 4.0%, 90% of RBCs after thawing showed integrity (FIG. 7A).

In an example of the present invention, materials to be cryopreserved may be bacteria, fungi, animal cells, plant cells, red blood cells, platelets, spermatocytes, oocytes, tissues, organs, or the like.

The composition of the present invention may protect cells constituting tissues and organs from being frozen.

The composition for cryoprotecting cells of the present invention may contain glycerol and/or DMSO.

In another example of the present invention, whether p-CY01_LM would substitute for glycerol as a cryoprotective agent in long-term cryopreservation was examined, and the percent hemolysis of red blood cells, which were cooled rapidly to −80° C. and preserved for 1 hour in an ADSOL containing 2.5% (w/v) p-CY01_LM, 1% (v/v) glycerol and 1% (v/v) DMSO (hereinafter, referred to as p-CY01_LM solution), was 6.09±0.64%, and the percent hemolysis after 5 months of preservation was 7.24±2.15%, indicating that there was little or no change in the percent hemolysis during 5 months of preservation (FIG. 7D).

In yet another aspect, the present invention is directed to a method for producing the exopolysaccharide which is produced by *Pseudoalteromonas* sp. strain CY01 (KCTC 12867BP) and which is composed of glucose and galactose, the method comprising the steps of: (a) culturing *Pseudoalteromonas* sp. strain CY01 (KCTC 12867BP) to produce the exopolysaccharide; and (b) recovering the produced exopolysaccharide.

In a further aspect, the present invention is directed to a method for producing the exopolysaccharide having a molecular weight of $1.0 \times 10^5$ to $4.3 \times 10^5$ Da, the method comprising the step of hydrolysis of the exopolysaccharide which is produced by *Pseudoalteromonas* sp. strain CY01 (KCTC 12867BP) and which is composed of glucose and galactose.

In the present invention, the hydrolysis may be weak acid decomposition.

In the present invention, the step of hydrolysis may further comprise performing a heat treatment.

In a still further aspect, the present invention is also directed to a method for cryopreserving cells using the above-described exopolysaccharide.

In the present invention, the freezing may be quick freezing which has a freezing rate ranging from 10° C./min to 196° C./min.

In a yet further aspect, the present invention is also directed to a *Pseudoalteromonas* sp. strain CY01 (KCTC 12867BP) which has the ability to produce a mucous exopolysaccharide. The *Pseudoalteromonas* sp. strain CY01 (KCTC 12867BP) may live in the *Antarctica*.

Figure 2:
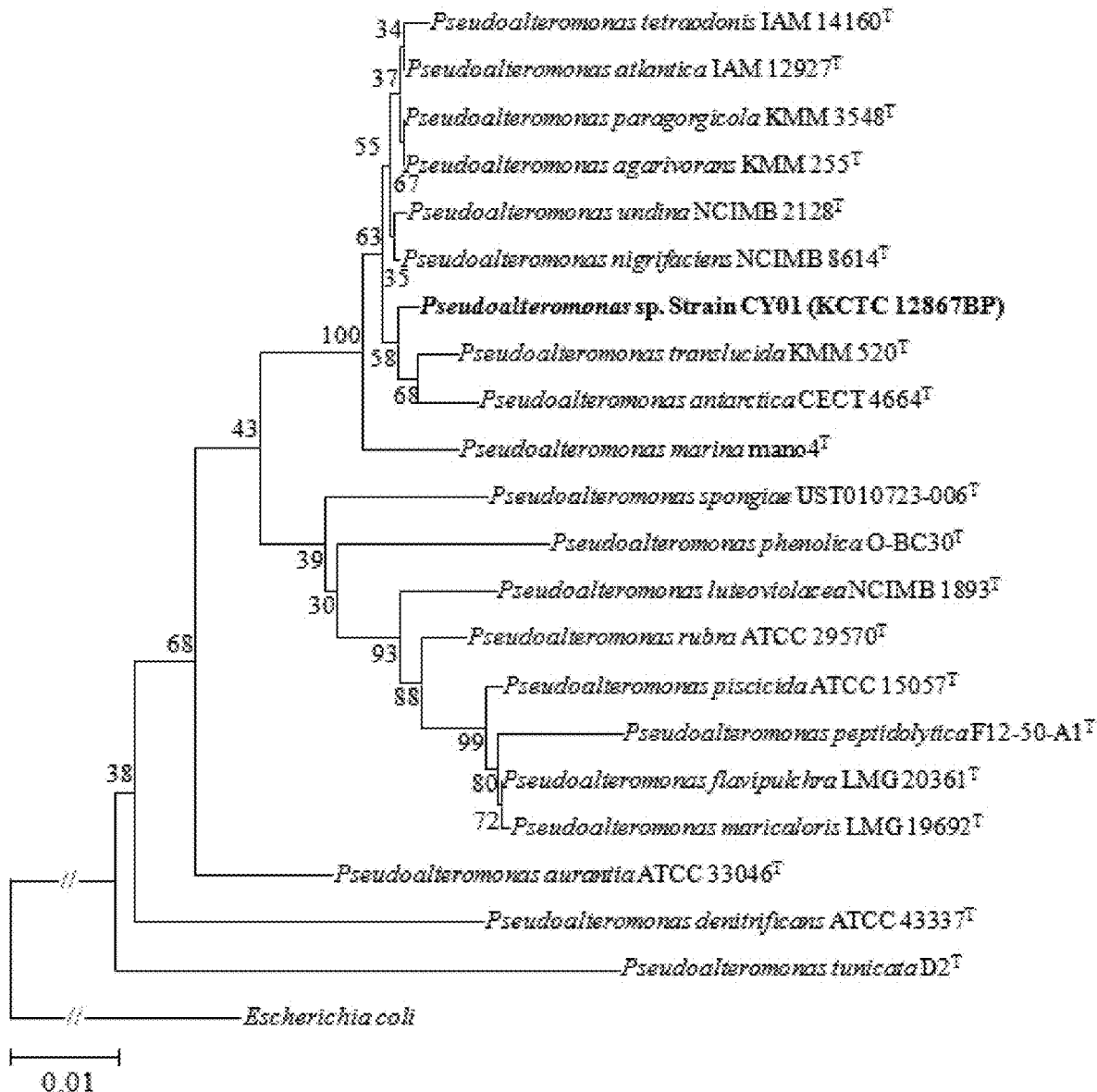
FIG. 2 shows the results of performing phylogenetic analysis using the 16S rRNA sequence of a CY01 strain.

Through phylogenetic analysis using the 16S rRNA sequence of the CY01 strain, the CY01 strain of the present invention was classified as a *Pseudoalteromonas* sp. strain that is abundantly present in the *Antarctica* (FIG. 2). The CY01 strain showed high homologies to *Pseudoalteromonas paragorgicola* KMM 3548T (99.52%), *P. nigrifaciens* NCIIMB 8614T (99.51%) and *P. agarivorans* KMM 255T (99.38%).

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Screening and Identification of Strain Producing Exopolysaccharide Having Cryoprotective Ability 2,980 strains isolated from Antarctic seawater samples were cultured using S-ZoBell (pH 7.0) agar plates (manufactured by the present inventors) at 15° C. for 3 days, and 73 strains producing mucous exopolysaccharides were isolated. To measure the amounts of exopolysaccharides produced by the isolated strains, the strains were cultured using S-ZoBell (pH 7.0) liquid media at 15° C. for 3 days, and exopolysaccharides were extracted and freeze-dried, and then the dry weights thereof were measured. The cryoprotective ability was measured by subjecting *E. coli* cells to freezing-thawing cycles in a 0.2% (w/w) crude exopolysaccharide solution obtained from each strain and then measuring the survival ratio of the *E. coli* cells.

Figure 1:
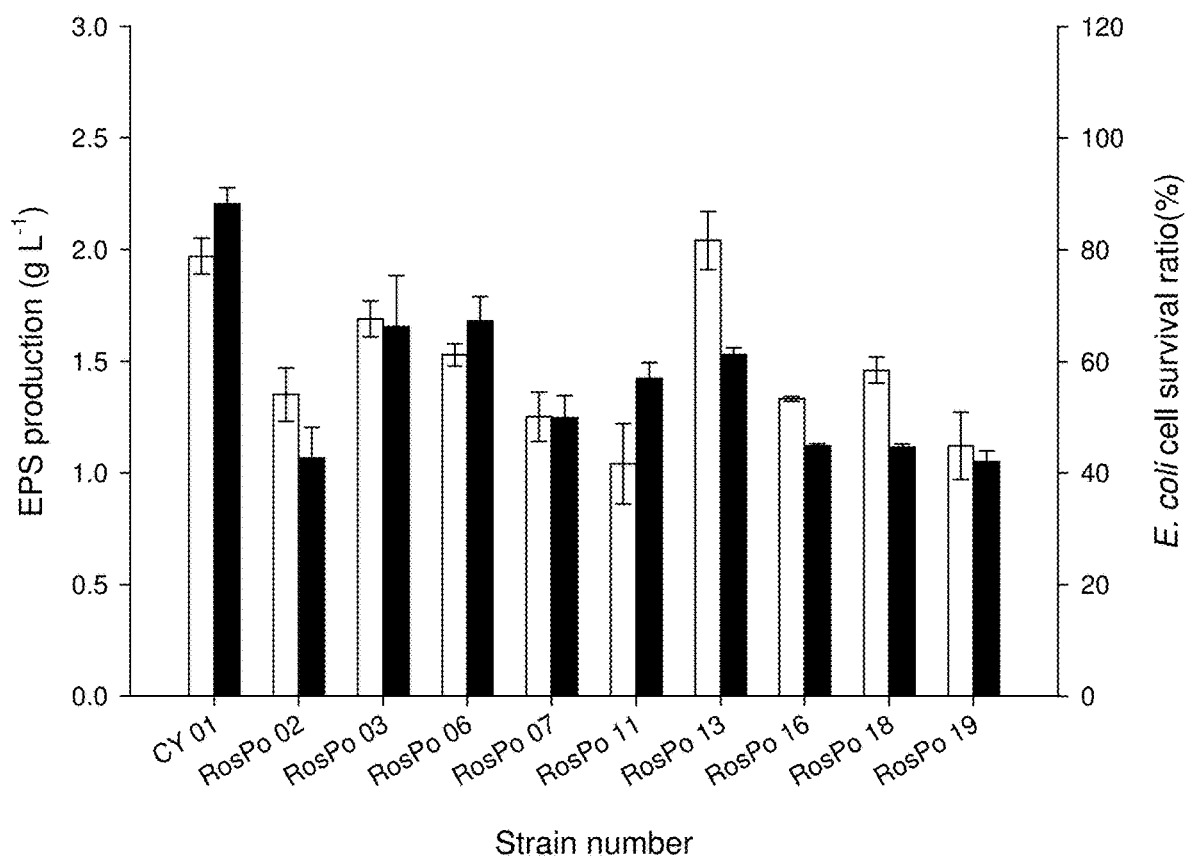
FIG. 1 shows the EPS production and cryoprotective effects of 10 isolated strains.

Among the isolated strains, 10 strains produced 1 g/L or more of crude exopolysaccharides (EPS), and the amounts of crude exopolysaccharides produced by these strains were in the range from 1.04±0.18 g/L to 2.04±0.13 g/L. Among the 10 strains, a RosPo13 strain showed the highest exopolysaccharide production (2.04 g/L), and the crude exopolysaccharide produced by a CY01 strain showed the highest cryoprotective ability (FIG. 1).

The survival ratio of *E. coli* cells in a solution containing 0.2% crude exopolysaccharide derived from the CY01 strain was 88.16±2.92%, and the survival ratios of *E. coli* cells in solutions containing 0.2% crude exopolysaccharides derived from other strains were 42.01±1.93% to 67.28±4.32%.

Through phylogenetic analysis using the 16S rRNA sequence of the CY01 strain, the CY01 strain was classified as a *Pseudoalteromonas* sp. strain that is abundantly present in the *Antarctica* (FIG. 2). The CY01 strain showed high homologies to *Pseudoalteromonas paragorgicola* KMM 3548T (99.52%), *P. nigrifaciens* NCIIMB 8614T (99.51%) and *P. agarivorans* KMM 255T (99.38%).

Figure 3A:
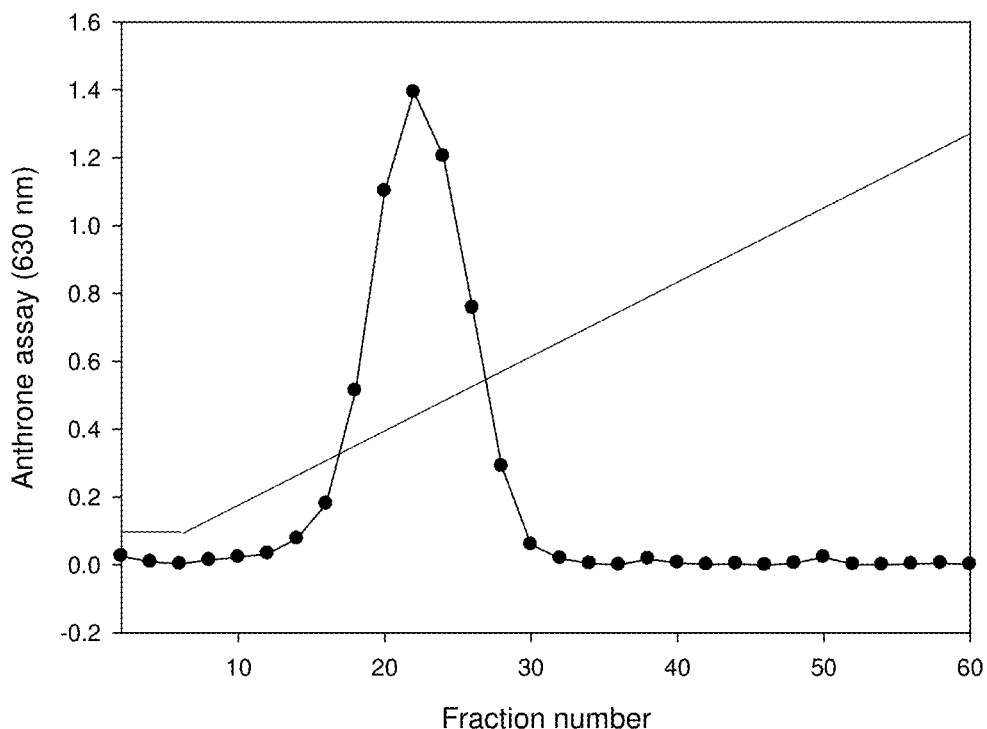
FIGS. 3A and 3B show the chromatographic peaks of CY01-derived EPS. Specifically.
Figure 3B:
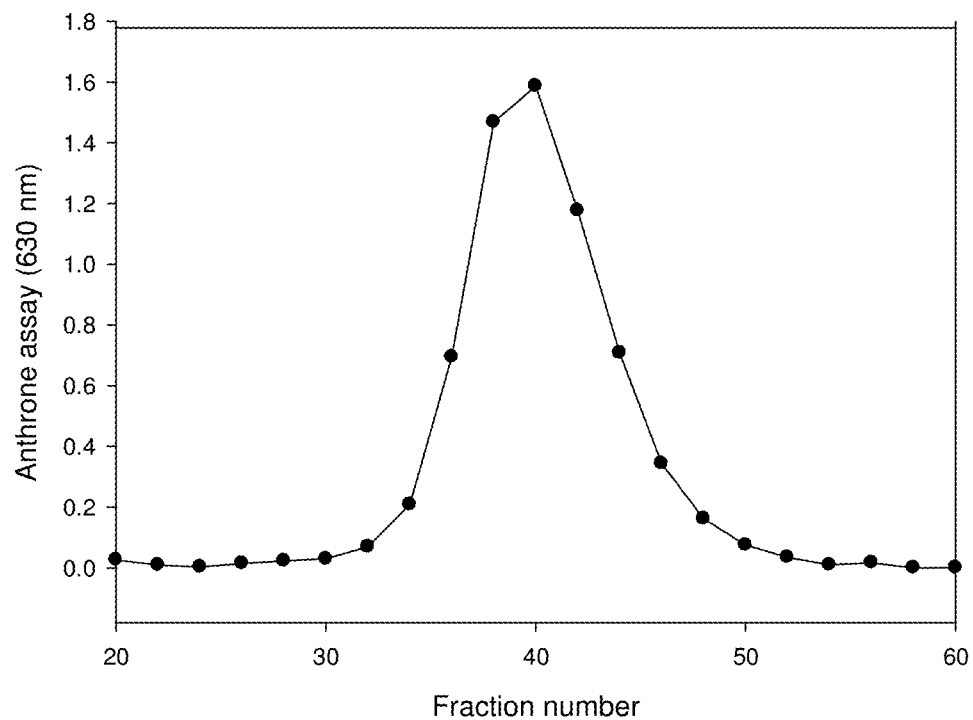

Example 2: Purification of Exopolysaccharide Derived from CY01 Strain and Characterization of Purified Exopolysaccharide An exopolysaccharide was separated from a culture of the CY01 strain by ethanol precipitation and treated with protease to remove protein. The obtained crude exopolysaccharide was subjected to anion chromatography using a DEAE-Sepharose column, thereby obtaining exopolysaccharide-containing fractions (FIG. 3A). The obtained exopolysaccharide fractions were purified by a Sepharose 4B-gel filtration chromatography column (FIG. 3B) to obtain a single fraction. The concentration of the exopolysaccharide in the fraction was measured at $OD_{630}$ by the Anthrone-sulfuric acid assay.

The obtained fraction was subjected to HPLC (Agilent, USA). HPLC was performed using 5 μl of a solution of the exopolysaccharide fraction in distilled water (0.1% w/w) at a flow rate of 0.4 ml/min, and detection was performed using an RI (Refractive index, Agilent, USA) detector.

Figure 4:
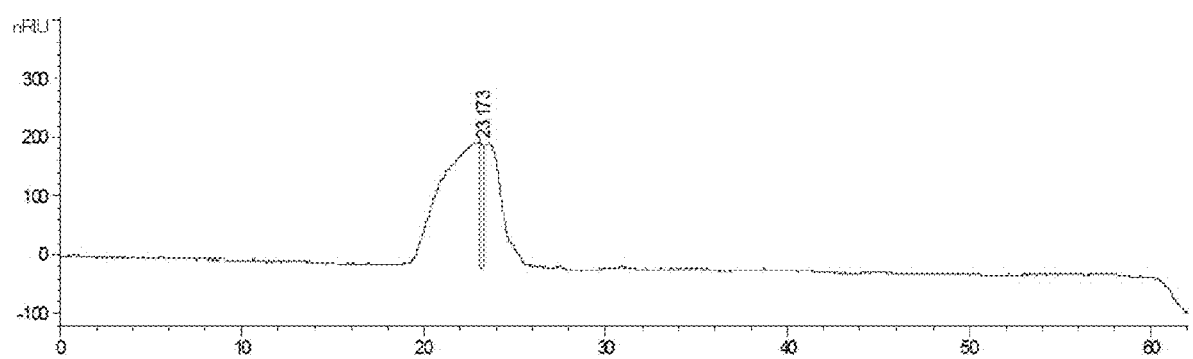
FIG. 4 shows the results of HPLC performed to analyze the purity of a CY01-derived EPS fraction obtained by gel filtration chromatography.

As a result, as shown in FIG. 4, a single peak was detected. The molecular weight of the exopolysaccharide purified by size-exclusion chromatography was measured using RI, and as a result, it was shown that the exopolysaccharide had an average molecular weight of about $1.1 \times 10^7$ Da. The purified EPS from the CY01 strain was named "p-CY01".

Using GC/MS, the sugar components of the exopolysaccharide were analyzed. The analysis was performed in electron impact ionization mode using Clarus 500 (Perkin-Elmer, USA) and a mass selective detector.

Figure 5A:
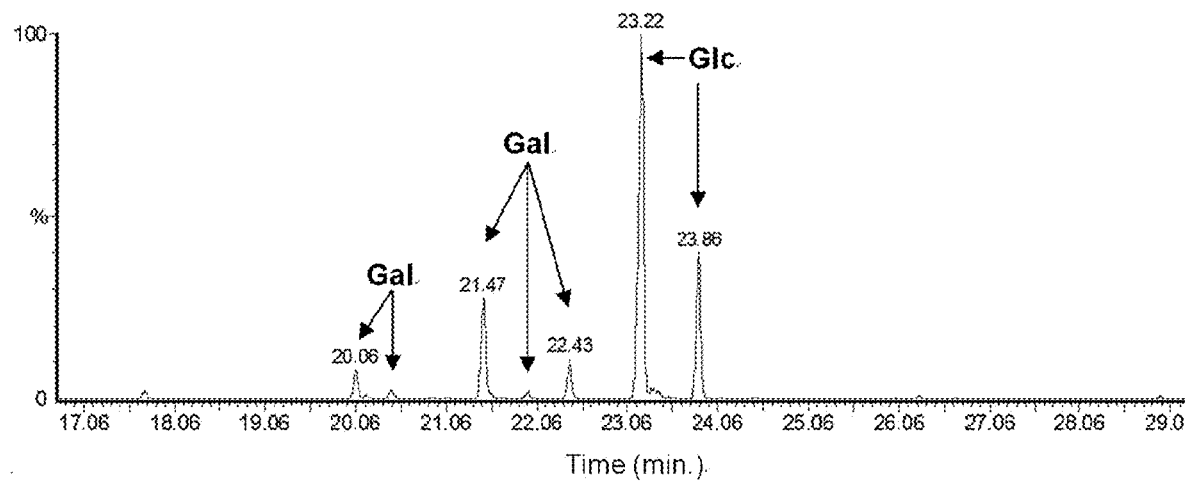
FIG. 5A shows the results of analyzing the sugar components of EPS by GS/MS.

As a result, as shown in FIG. 5A, p-CY01 was composed of glucose and galactose, and glucose was a predominant sugar component in p-CY01. Moreover, the molar ratio of glucose:galactose in p-CY01 was about 3.4:1.

Figure 5B:
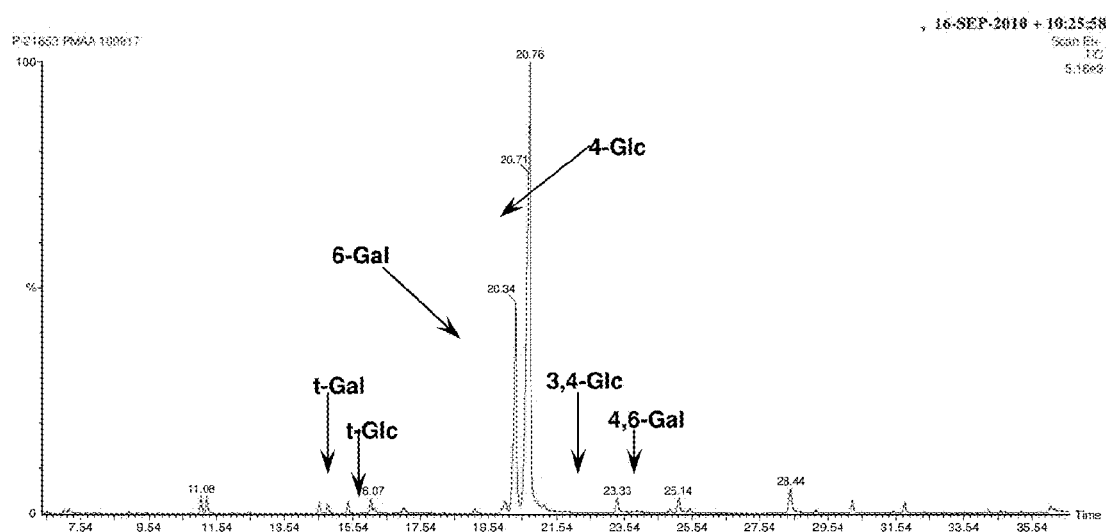
FIG. 5B shows the results of analyzing the bonding patterns of the sugar components of EPS by GC/MS.

As shown in FIG. 5B and Table 1 below, the results of glycosyl linkage analysis of p-CY01 indicated that p-CY01 consisted mainly of 4-linked glucopyranose and 6-linked galactopyranose. As minor peaks, end-linked galactopyranose, end-linked glucopyranose, 3,4-linked glucopyranose and 4,6-linked galactopyranose were detected.

TABLE 1

Analysis of glycosyl linkage components of exopolysaccharide p-CY01 derived from CY01 strain

| Methylated sugars | Rt (min) | Molar ratio | Mode of linkage |
|---|---|---|---|
| 2,3,4,6-Me$_4$-Galp | 16.08 | 0.02 | $^1$Gal (T)$^\alpha$ |
| 2,3,4,6-Me$_4$-Glcp | 17.04 | 0.01 | $^1$Glc (T)$^\alpha$ |
| 2,3,4-Me$_3$-Galp | 20.35 | 0.35 | $^1$Gal$^6$ |
| 2,3,6-Me$_3$-Glcp | 20.6 | 1 | $^1$Glc$^4$ |
| 2,6-Me$_2$-Glcp | 23.33 | 0.03 | $^1$Glc$^{3,4}$ |
| 2,3-Me$_2$-Galp | 25.11 | 0.02 | $^1$Gal$^{4,6}$ |

For p-CY01, 1D and 2D NMR experiments for determining structures were performed using a Bruker AVANCE (600 MHz) spectrometer. Samples were measured at 25° C., $^1$H NMR was measured at 600 MHz, and $^{13}$C NMR was measured at 150 MHz.

Figure 6A:
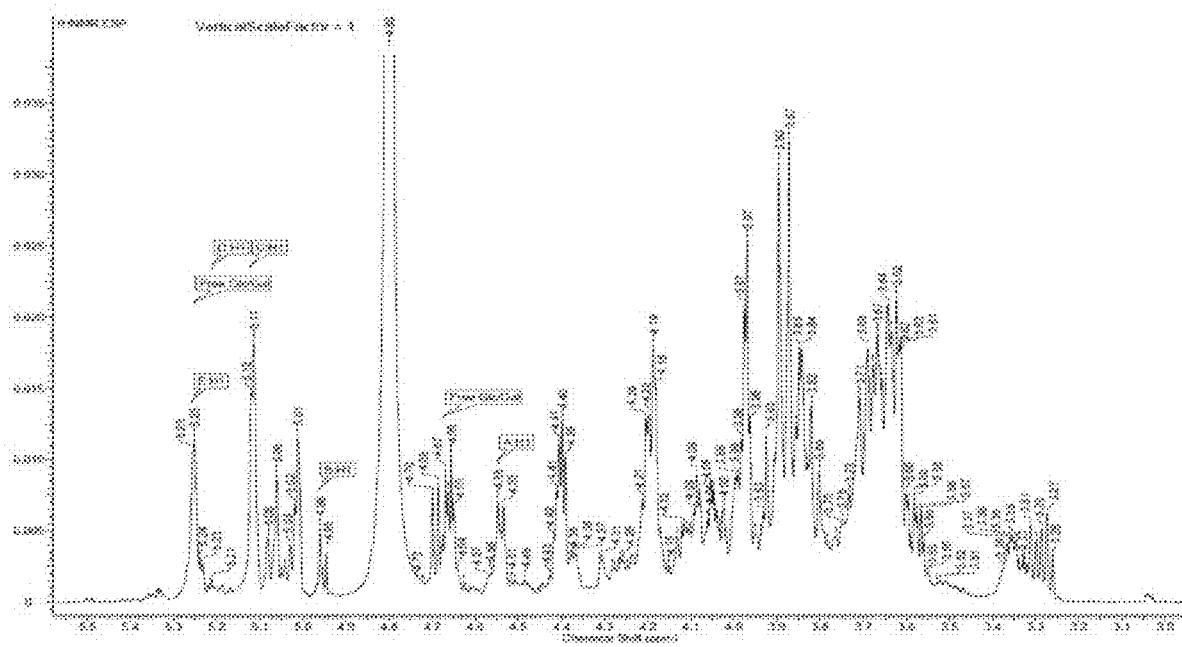
FIGS. 6A and 6B show the $^1$H and $^{13}$C NMR spectra of p-CY01_LM obtained by low molecularization of p-CY01.
Figure 6B:
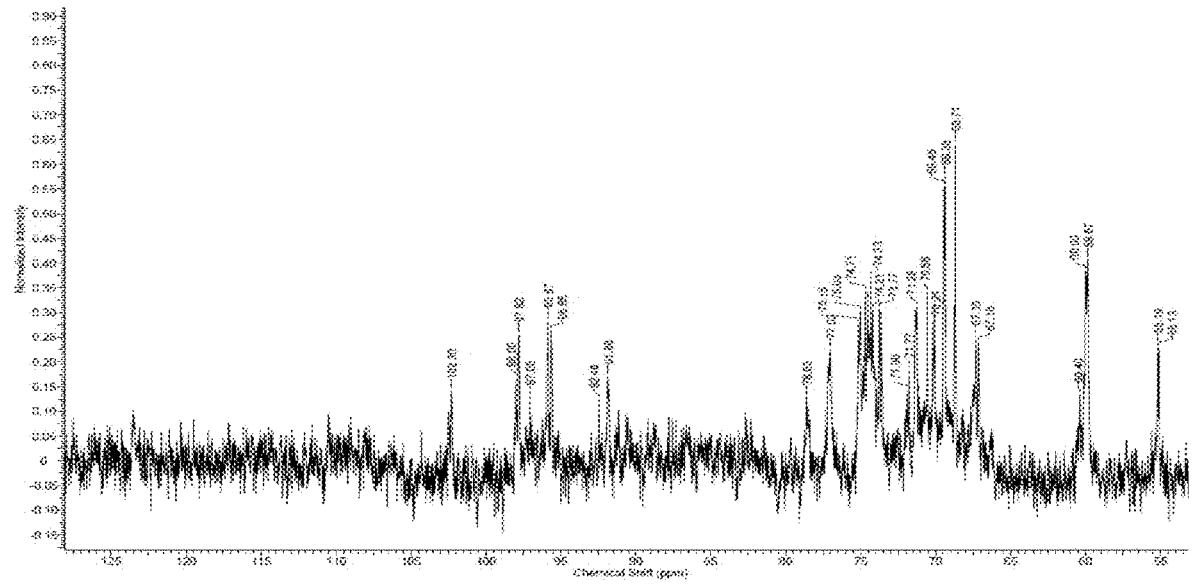
Figure 8:
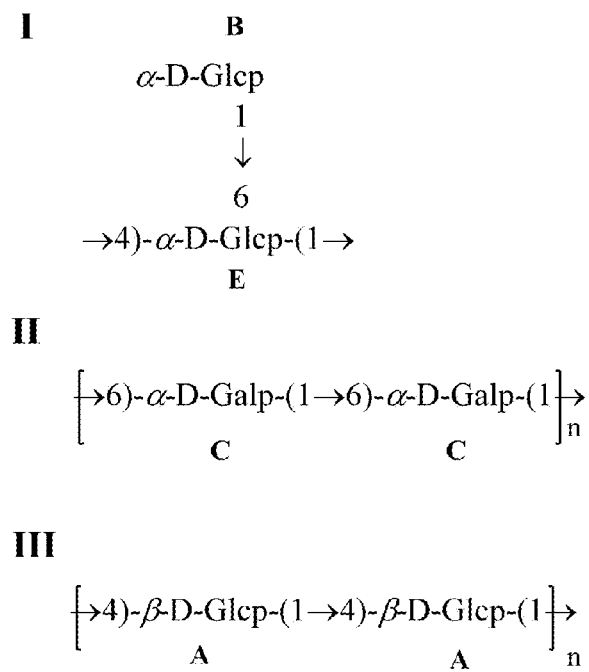
FIG. 8 shows the results of analyzing the main structures of p-CY01 based on the GC/MS and NMR analysis results.

Through NMR analysis, the typical peak patterns of polyglucopyranose and polygalactopyranose could be seen from the $^1$H and $^{13}$C NMR spectra of p-CY01 (FIGS. 6A and 6B). Particularly, it was observed that p-CY01 was composed mainly of a repeating unit of →4)-β-D-Glcp-(1→ and →6)-α-D-Galp-(1→, and the peaks of other side chains were relatively small or did overlap with the peaks of the main repeating units. In addition, from the 2D-HSQC spectra (FIGS. 7A and 7B), proton-carbon correlation was observed, but from 2D-TOCSY, 2D-COSY, 2D-HMBC and 2D-NMR (600 MHz), unusual information other than the correlation of glucopyranose and galactopyranose which are the main components could hardly be observed (FIGS. 7C through 7F). Taking the glycosyl linkage analysis results and the NMR spectrum analysis results together, the main structures of p-CY01 were determined (FIG. 8). As can be seen from the analysis results, p-CY01 has a repeating structure consisting mainly of 4-linked glucopyranose and 6-linked galactopyranose, and a linkage structure of [→4)-β-D-Glcp-(1→4)-β-D-Glcp-(1→]n of III and a linkage structure of [→6)-α-D-Galp-(1→6)-α-D-Galp-(1→]n of II are repeatedly connected to each other to form the main chain. In addition, it was shown that p-CY01 has a small amount of a linkage structure of T-α-D-Glcp-(1→6)-α-D-Glcp-(1,4→ of I as the side chain structure of the main chain.

Example 3: Analysis of Changes in Molecular Weight and Rheological Properties of Exopolysaccharide after Hydrolysis Because the high viscosity and low solubility of the exopolysaccharide may interfere with the application of the exopolysaccharide in the biological industry, the reduction in average molecular weight of the polymer by decomposition can reduce the viscosity and increase the solubility. Recently, when oocytes and red blood cells were cryopreserved using a high concentration of PVA, there were disadvantages in that handling is not easy due to the high viscosity of the solution and washing needs to be performed (Deller, R C et al., *Nat. Commun.*, 5:3244, doi:10.1038/ncomms4244, 2014).

Figure 9A:
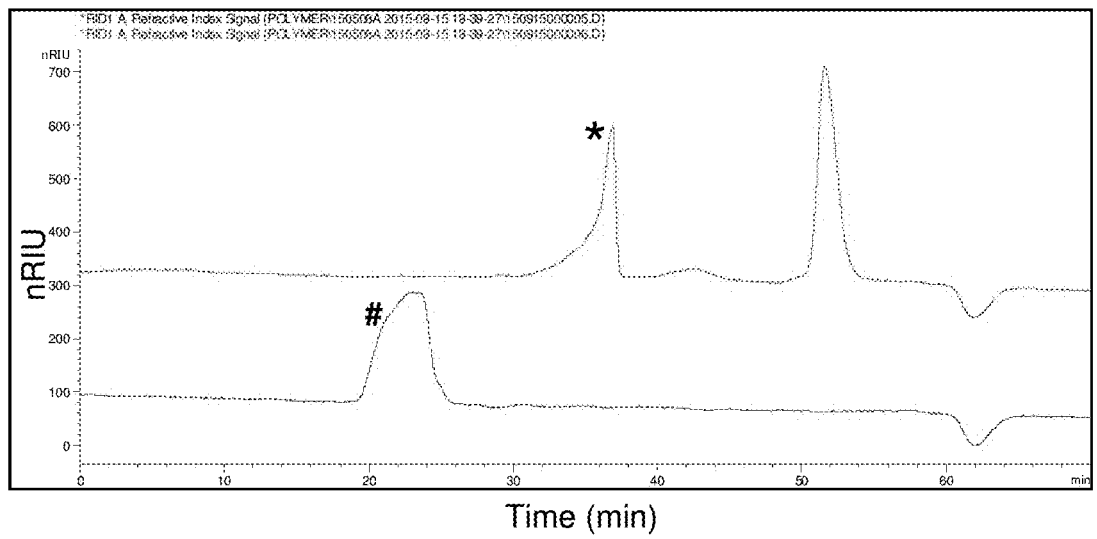
FIG. 9A shows the results of size exclusion chromatography of p-CY01 and p-CY01_LM obtained by acid decomposition treatment and FIG. 9B shows changes in the rheological properties of p-CY01_LM solution. # indicates p-CY01, and * indicates p-CY01_LM.

In this Example, in order to overcome such disadvantages of the polymer, the molecular weight of p-CY01 of the present invention was regulated by weak acid decomposition. p-CY01 was heated together with 0.1 M of TFA (trifluoroacetic acid) at 121° C. for 1 hour to obtain acid-decomposed p-CY01, and gel permeation chromatography (GPC) was performed. As a result, p-CY01 not treated with TFA was eluted from the GPC column between 19 min and 25 min, and in the case of p-CY01 heat-treated with TFA, the main peak was eluted at 33 min and 37 min and also eluted at 51 min (FIG. 9A). The high-molecular-weight peaks at 33 min and 37 min were fractions resulting from partial decomposition of p-CY01, and the peak appearing at 51 min was a monosaccharide resulting from decomposition of p-CY01. The average molecular weight of p-CY01 was about $1.1 \times 10^7$ Da, whereas the molecular weight of p-CY01_LM partially decomposed by acid was $1.0 \times 10^5$ to $4.3 \times 10^5$ Da.

Changes in the rheological properties of the low-molecular p-CY01 (p-CY01_LM) solution were measured.

The rheological properties were measured by a Brookfield viscometer using spindle S18, and the shear stresses of p-CY01, PBS and p-CY01_LM solutions (0.2%, 2.5% and 5.0%, w/v) at different shear rates were measured.

Figure 9B:
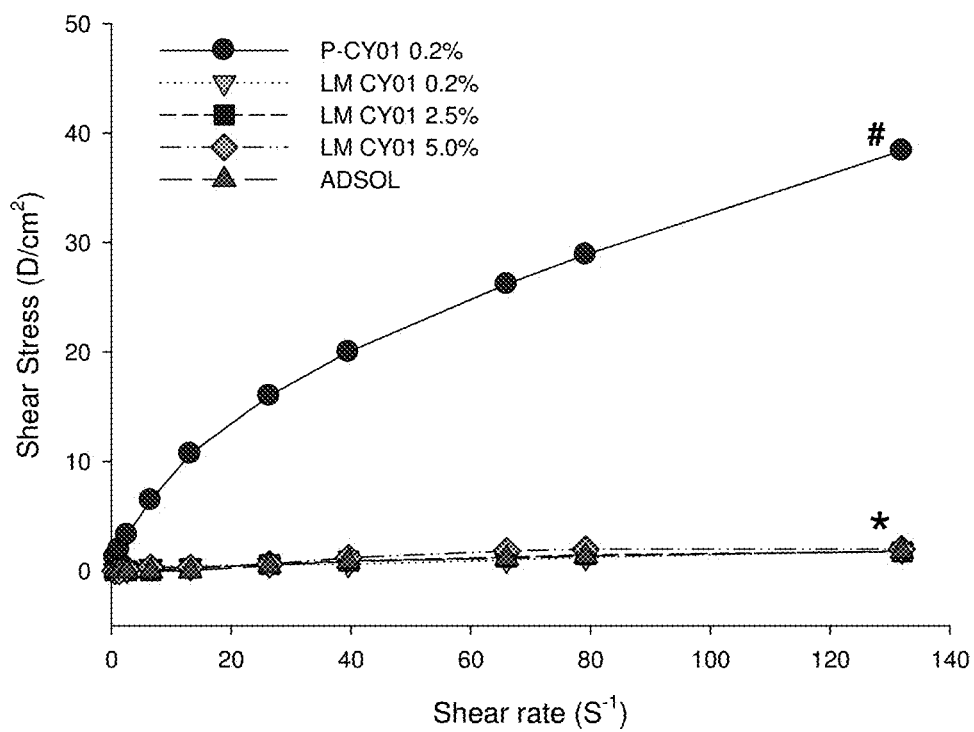

As a result, as shown in FIG. 9B, in the case of 0.2% p-CY01 solution, the shear rate increased as the shear rate increased, but in the case of p-CY01_LM solution, the shear stress did not increased at high shear rate. This indicates that the viscosity of p-CY01_LM significantly decreased. This decrease in the viscosity is attributable to a change in the molecular weight of p-CY01. As the exopolysaccharide is decomposed and depolymerized, the viscosity decreases and the solubility increases.

Example 4: Cryopreservation of Human Red Blood Cells (RBCs) in p-CY01_LM

Red blood cells can be preserved in ADSOL at 4° C. for 32 days. When red blood cells are deglycerolized in Haemonetics ACP215 and preserved in ADSOL, these cells can be preserved at 4° C. for 3 days while having a hemolysis ratio of less than 1%. Glycerol is an intracellular cryoprotective agent, and in order to prevent the hemolysis of red blood cells, the final concentration of glycerol should be reduced to 1% by washing after thawing.

DMSO was approved by the FDA for use as a cryoprotective agent for human platelets and red blood cells. Thus, in the following cryopreservation experiment using p-CY01_LM, glycerol and DMSO were used together, and ADSOL was used as a cryopreservative buffer instead of PBS.

In clinical practice, when red blood cells are cooled with a high concentration (40%) of glycerol at a low cooling rate (1° C./min) and preserved at −80° C. or in liquid nitrogen, high red blood cell recovery can appear. In addition, exopolysaccharides cryoprotective agents (PVP, HES) require physical freezing and preservation in liquid nitrogen.

In this Example, a red blood cell sample was frozen without controlling cooling rate (cooled immediately to −80° C.) and preserved at −80° C. The red blood cell sample was rapidly thawed in a water bath at 40° C. After thawing, the hemolysis of the sample was quantified by the Drabkin's assay.

The function of p-CY01_LM as a cryoprotective agent was analyzed by a red blood cell hemolysis assay and optical microscopic analysis.

Figure 10A:
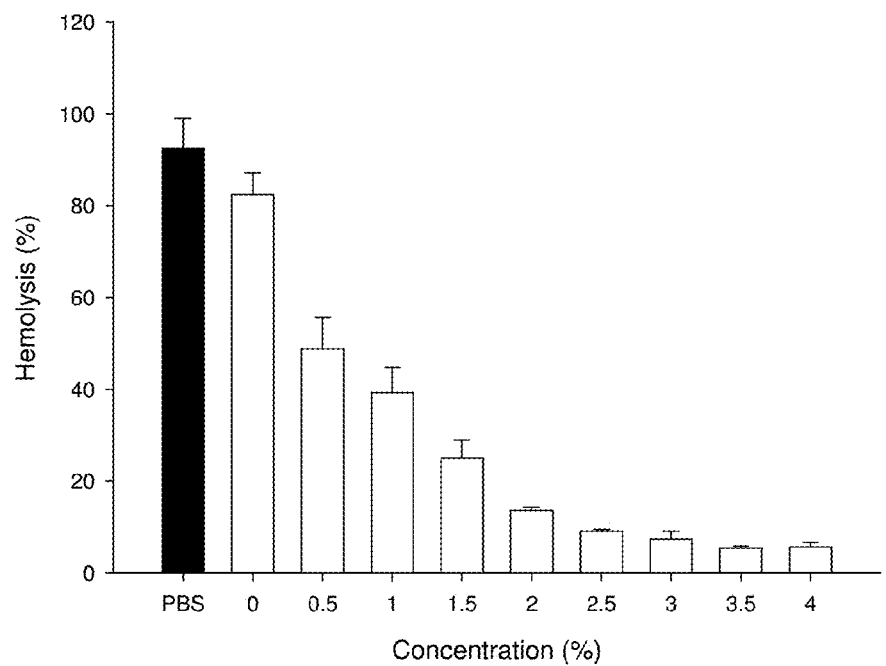
FIG. 10A shows the hemolysis (%) of red blood cells as a function of the concentration of p-CY01_LM in a cryopreservation medium.

As can be seen in FIG. 10A, the hemolysis (%) decreased as the concentration of p-CY01_LM increased. At a p-CY01_LM concentration of 2.5% to 4.0%, a percent hemolysis of 9.08±0.37% to 5.64±0.96% appeared, and the use of 3.5% p-CY01_LM showed the lowest hemolysis (5.40%). In other words, it was shown that, at a p-CY01_LM concentration of 2.5% to 4.0%, 90% of RBCs after thawing showed integrity. The standards of the American Association of Blood Bank require an immediate survival rate of 80% (a hemolysis of less than 20%) and require that 70% of blood cells should survive for 24 hours.

Figure 10B:
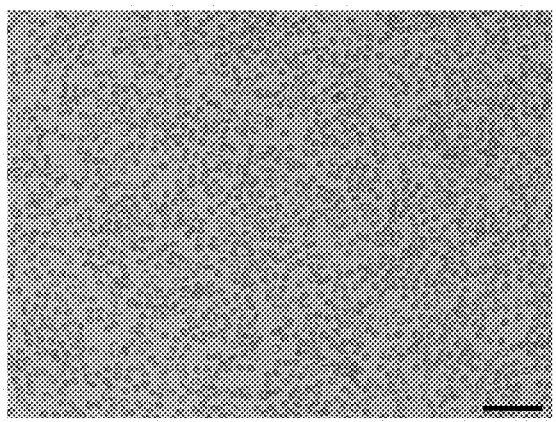
FIG. 10B shows the results of microscopic observation performed to confirm the integrity of red blood cells thawed after cryopreservation in 2.5% p-CY01_LM solution.
Figure 10C:
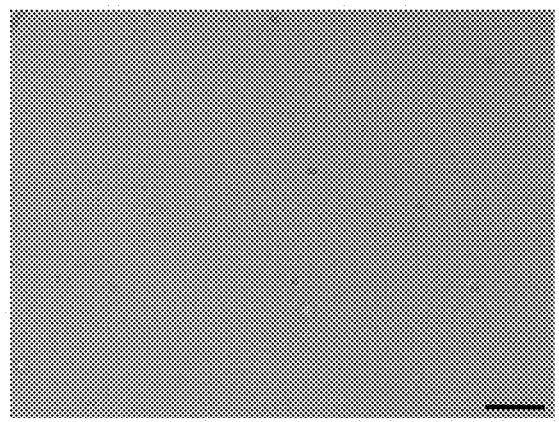
FIG. 10C shows the results of analyzing the integrity of red blood cells thawed after cryopreservation in PBS solution.

An ADSOL solution containing 2.5% (w/v) p-CY01_LM, 1% (v/v) glycerol and 1% (v/v) DMSO showed a percent hemolysis of 9.08±0.37% (a red blood cell integrity after thawing of 90.92%) (FIGS. 10A and 10B), and PBS showed a percent hemolysis of 92.48±6.49% (a red blood cell integrity after thawing of 7.52%) (FIGS. 10A and 10C).

Therefore, 2.5% p-CY01_LM was selected as the optimum concentration of cryopreservation of red blood cells.

Figure 10D:
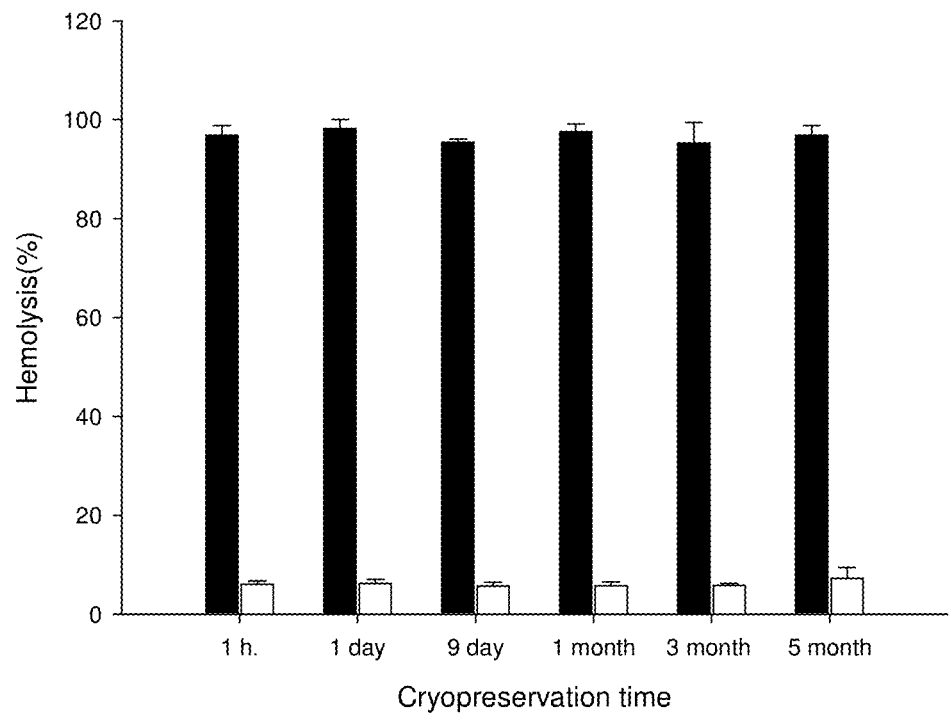
FIG. 10D shows the hemolysis (%) of red blood cells thawed after long-term cryopreservation in p-CY01_LM solution.

Whether p-CY01_LM would substitute for glycerol as a cryoprotective agent in long-term cryopreservation was examined. As shown in FIG. 10D, the percent hemolysis of red blood cells, which were cooled rapidly to −80° C. and preserved for 1 hour in an ADSOL containing 2.5% (w/v) p-CY01_LM, 1% (v/v) glycerol and 1% (v/v) DMSO (hereinafter, referred to as p-CY01_LM solution), was 6.09±0.64%, and the percent hemolysis after 5 months of preservation was 7.24±2.15%, indicating that there was little or no change in the percent hemolysis during 5 months of preservation.

In addition, the percent hemolysis of red blood cells preserved in the p-CY01_LM solution at room temperature for 1 hour was maintained at less than 2% (a red blood cell integrity of more than 98%), indicating that cytotoxicity or hemolysis did not occur during cryopreservation.

Example 5: Measurement of Biochemical Properties of Red Blood Cells Frozen with p-CY01_LM The ATP level of red blood cells makes it possible to determine whether the concave shape of the red blood cell membrane would be maintained and whether the dynamics of the red blood cell membrane would increase. The ATP level and the 2,3-DPG (2, 3-diphosphoglycerate) that controls the oxygen affinity of hemoglobin were measured to determine cell function and the therapeutic usefulness of red blood cells.

The ATP and 2, 3-DPG activities of a hemolysate of fresh red blood cells as a positive control group were measured, and the ATP and 2, 3-DPG activities of a hemolysate of red blood cells cryopreserved in the p-CY01_LM solution at −80° C. for 1 hour, as a test group, were measured.

Figure 11:
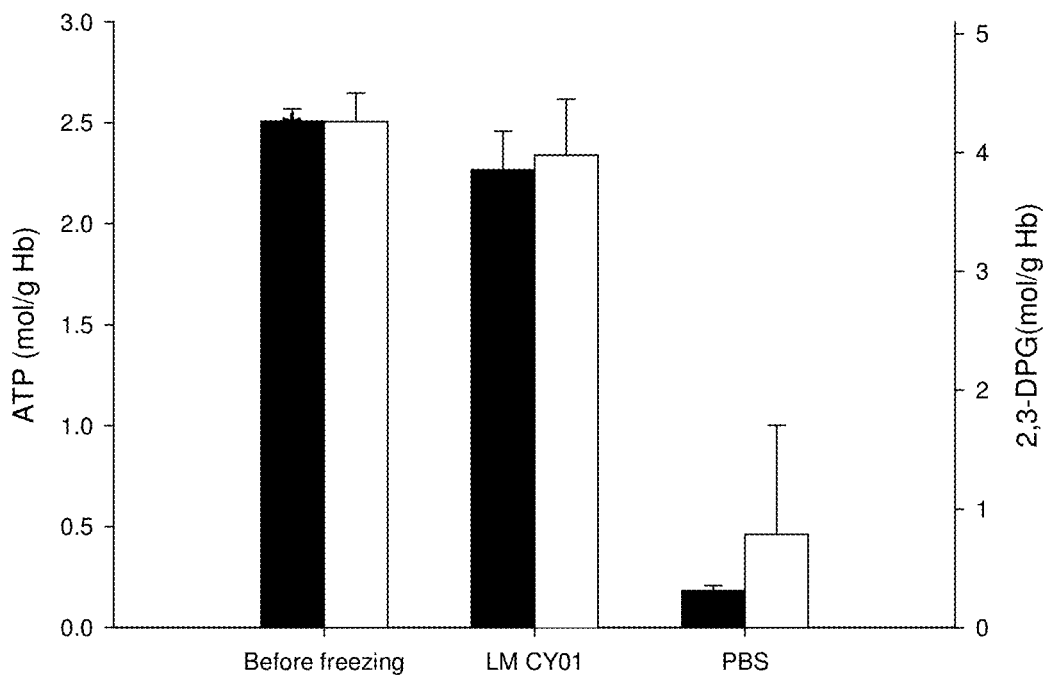
FIG. 11 shows the results of measuring ATP and 2, 3-DPG activities after hemolysis of red blood cells cryopreserved in p-CY01_LM solution.

As a result, as shown in FIG. 11, the red blood cells cryopreserved in the p-CY01_LM solution showed little or no difference in ATP activity from the positive control group. The ATP activity of the red blood cells cryopreserved in the p-CY01_LM solution was 2.50±0.06 μmol/gHb to 2.26±0.19 μmol/gHb, and the ATP activity of red blood cells cryopreserved in PBS as a negative control group greatly decreased to 0.18±0.02 μmol/gHb. The concentration of 2,3-DPG was 4.26±0.24 μmol/gHb in the fresh red blood cells, 3.98±0.47 μmol/gHb in the red blood cells cryopreserved in the p-CY01_LM solution, and 0.78±0.92 μmol/gHb in the red blood cells cryopreserved in PBS.

There was no significant difference in ATP activity and 2, 3-DPG concentration between the fresh red blood cells and the red blood cells cryopreserved in the p-CY01_LM solution.

Example 6: Examination of Main Cryoprotective Additives and Analysis of Main Effects on Cryopreservation of Red Blood Cells In order to analyze the effect of each cryoprotective agent on cryopreservation of red blood cells, the red blood cell preservation ability of each of ADSOL alone, a solution containing 1% (w/v) glycerol and 1% (w/v) DMSO (G+D), a 2.5% (w/v) p-CY01_LM solution, and a solution containing 1% (w/v) glycerol, 1% (w/v) DMSO and 2.5% (w/v) p-CY01_LM (G+D+p-CY01_LM), was measured based on the percent hemolysis of red blood cells.

Figure 12A:
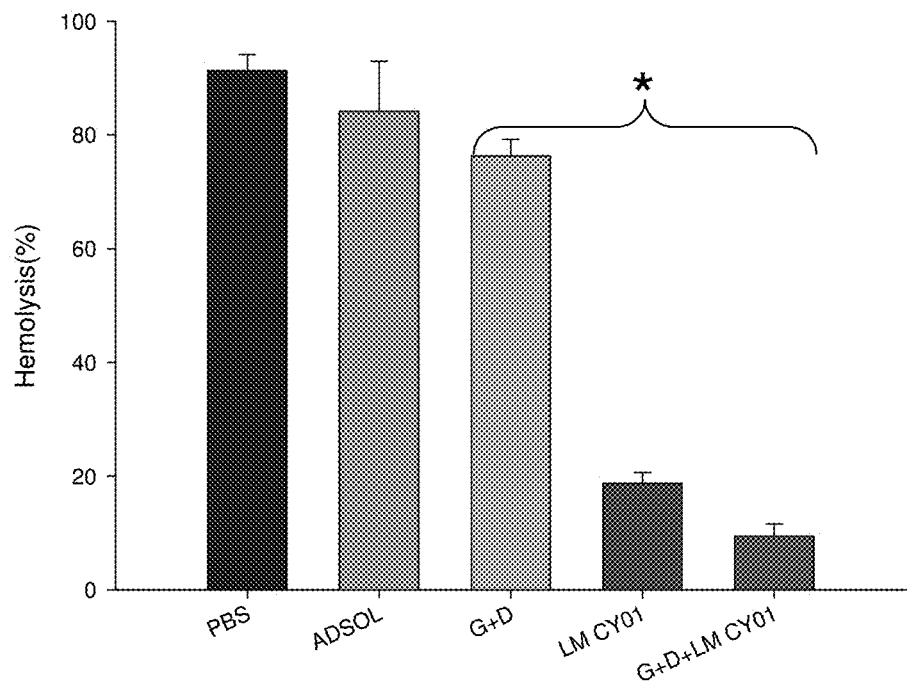
FIG. 12A shows the results of analyzing the red blood cell preservation ability of each component added to a cryopreservation medium.

As a result, as shown in FIG. 12A, the percent hemolysis of red blood cells in the solution containing 1% (v/v) glycerol and DMSO was 76.29±2.95%, which did not greatly differ from the percent hemolysis in the negative control PBS or ADSOL. Furthermore, the solution containing 2.5% (w/v) p-CY01_LM alone showed a significantly low red blood cell hemolysis of 18.73±1.86%. In addition, the solution containing 1% (w/v) glycerol, 1% (w/v) DMSO and 2.5% (w/v) p-CY01_LM showed a percent hemolysis of 9.43±2.16%, indicating that this solution exhibited the best cryoprotective effect.

Using the Packett-Burman method, the main effect value of each cryoprotective component on cryopreservation of red blood cells was calculated.

Figure 12B:
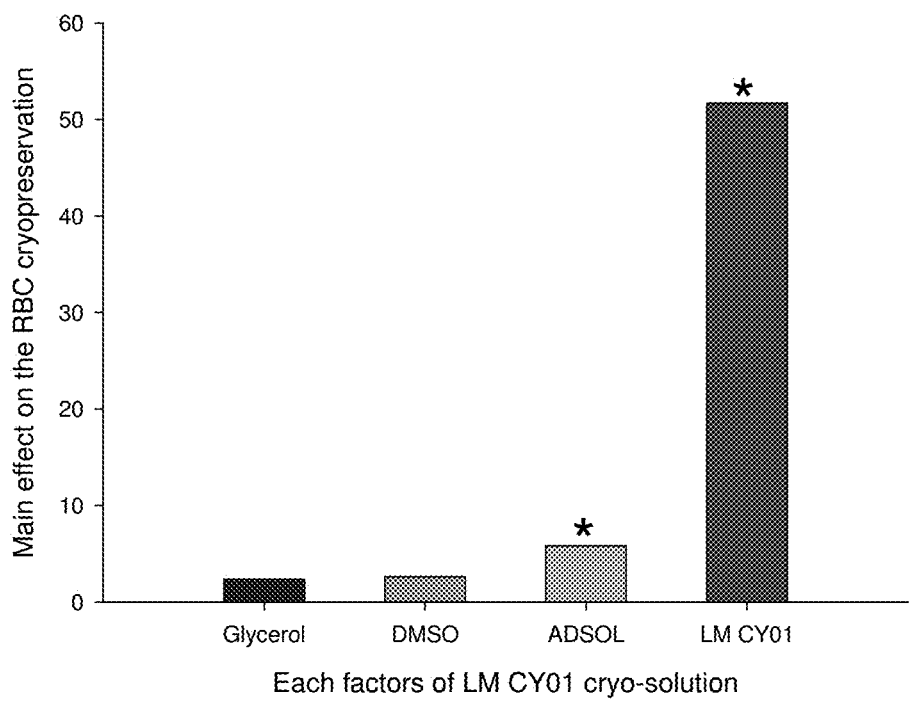
FIG. 12B shows the results of Plackett-Burman statistical analysis performed to analyze the main effect of each component, which is added to a cryopreservation medium, on cryopreservation of red blood cells. * indicates that statistically different values are equal to or smaller than 0.05.

As shown in FIG. 12B and Table 2 below, 1% glycerol, 1% DMSO, ADSOL and 2.5% (w/v) p-CY01_LM showed positive main effect values on cryopreservation of red blood cells. The main effect values were 2.32 for glycerol, 2.62 for DMSO, 5.82 for ADSOL, and 51.69 for p-CY01_LM, indicating that even though the concentration of p-CY01_LM used in cryopreservation of red blood cells was only 2.5 times that of glycerol or DMSO, the main effect of p-CY01_LM on cryopreservation of red blood cells was at least 19 times that of glycerol or DMSO. The P-values of ADSOL and p-CY01_LM were 0.05 or below, which was significant compared to that of glycerol or DMSO.

TABLE 2

Statistical analysis of cryoprotective components using Plackett-Burman design

| Variables | Effect | S.E. | t-statistics | P-value |
|---|---|---|---|---|
| Glycerol | 2.321 | 0.9096 | 1.28 | 0.224 |
| DMSO | 2.621 | 0.9096 | 1.44 | 0.173 |
| ADSOL | 5.826 | 0.9096 | 3.20 | 0.007 |
| p-CY01_LM | 51.694 | 0.9096 | 28.41 | 0.000 |

Example 7: Differential Scanning Calorimetry (DSC) Analysis of p-CY01_LM

Figure 13A:
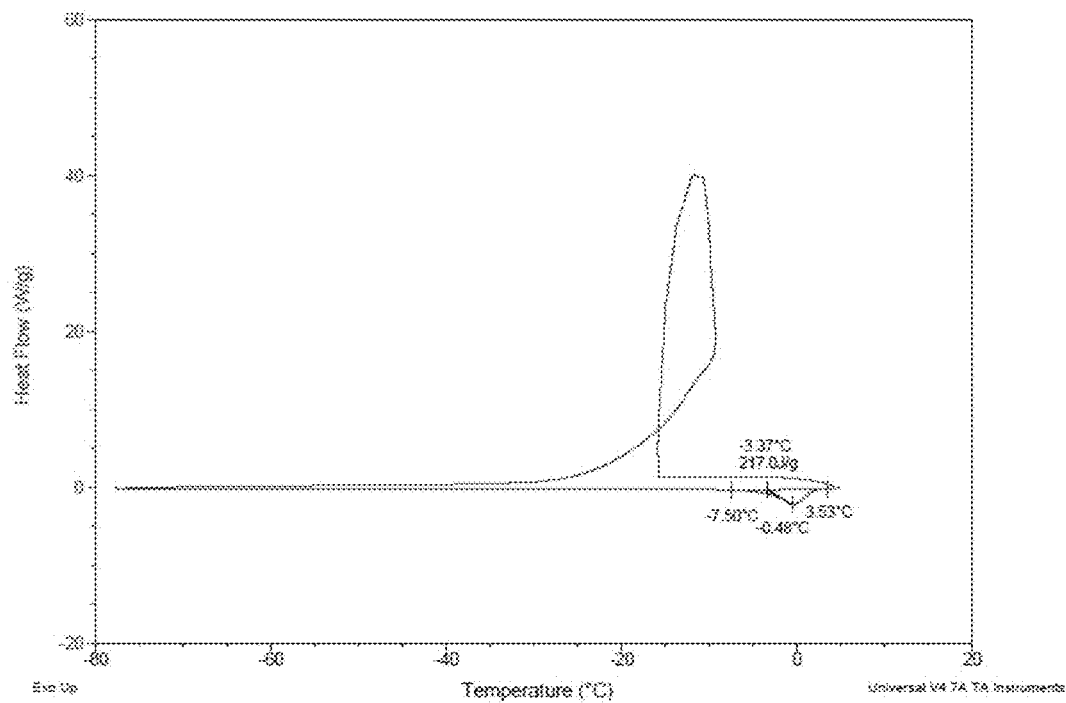
FIGS. 13A through 13C show the results of DSC analysis of p-CY01_LM solution. Specifically.
Figure 13B:
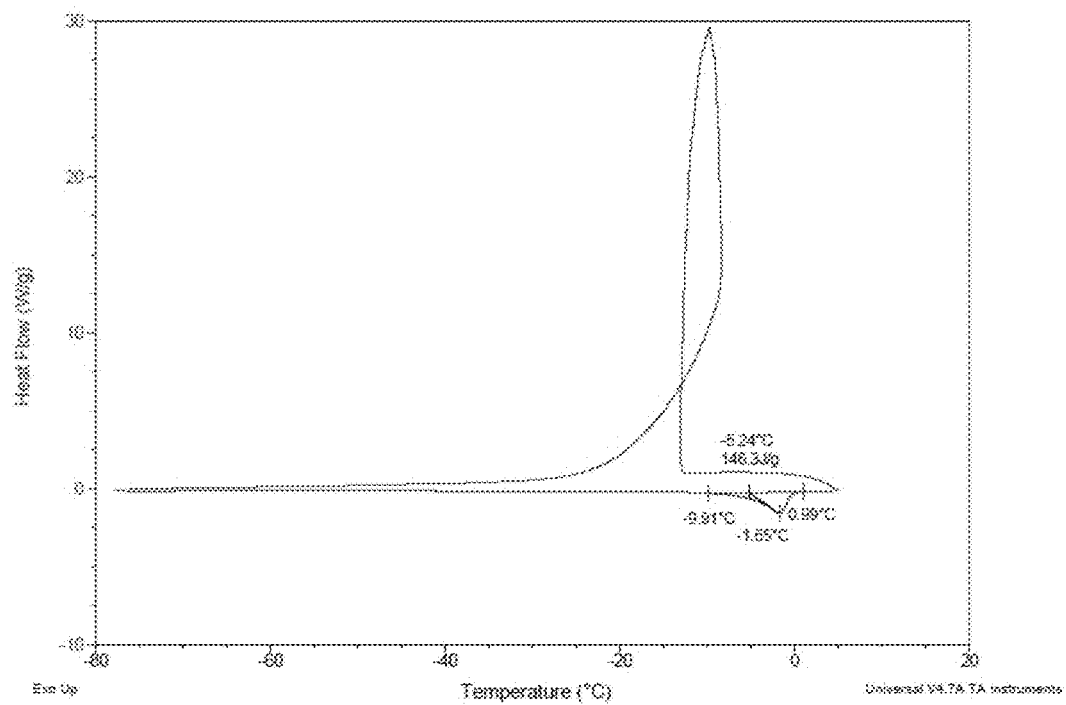
Figure 13C:
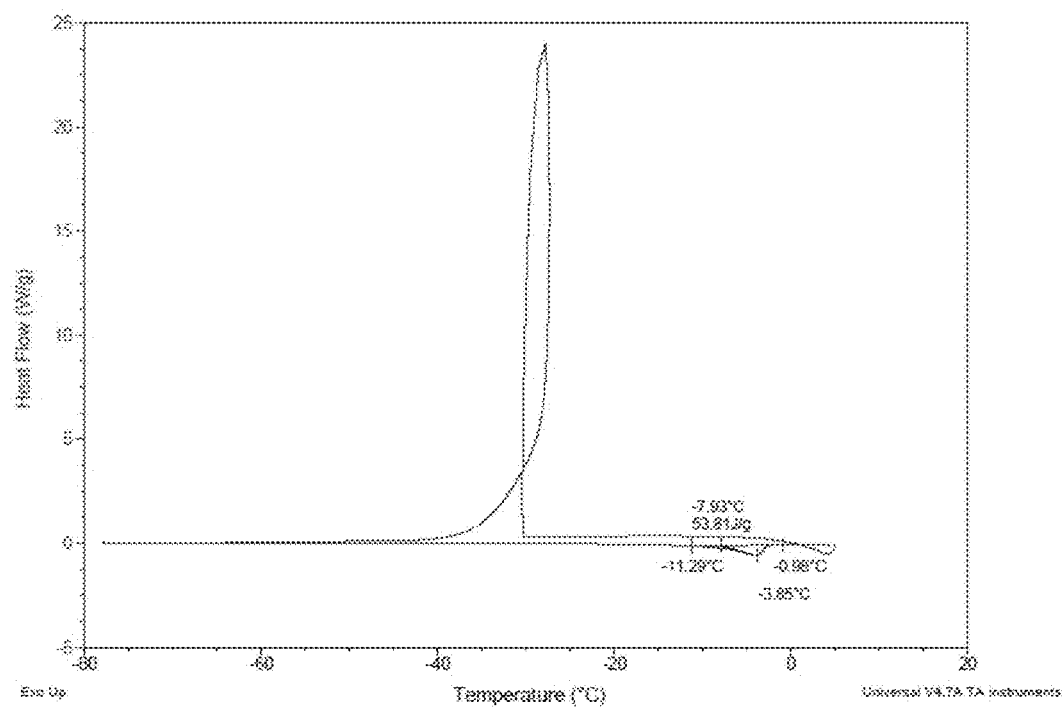

DSC analysis of the p-CY01_LM solution in cooling and thawing was performed (FIGS. 13A through 13C). Each sample was cooled from +5° C. to −78° C. at a rate of 40° C./min and thawed at a rate of 2° C./min.

For a solution containing 1% glycerol and 1% DMSO (FIG. 13A) and solutions containing 1% glycerol, 1% DMSO and 0.5 to 2.5% p-CY01_LM (FIGS. 13B and 13C), DSC analysis was performed. When a solution containing low concentrations (less than 1%) of glycerol and DMSO, which is a negative control, was used, the change in enthalpy ($\Delta H(J/g)$) was 212.0±3.8 (J/g), which was significantly low like a cryoprotective mechanism which occurred when high concentrations (10 to 40%) of glycerol and DMSO were used in the prior art, indicating that the solution did not act to reduce the amount of ice formed during freezing (Table 3). The super cooling point of the solution containing 1% glycerol and 1% DMSO was −14.2° C., and the super cooling point of the solution containing 1% glycerol, 1% DMSO and 0.5% p-CY01_LM was −13.9° C., and the super cooling point of the solution containing 1% glycerol, 1% DMSO and 2.5% p-CY01_LM was −32.1° C. Table 3 below shows the changes in enthalpy of each test group as a function of freezing and thawing temperatures. Freezing and thawing temperatures in the case of the solution containing 1% glycerol, 1% DMSO and 2.5% p-CY01_LM were significantly lowered, and the change in enthalpy $\Delta H(J/g)$ significantly decreased to 52.81±8.7 (J/g) (Table 3). This phenomenon means that the total amount of water that can be formed into ice during freezing-thawing cycles is reduced. In addition, this phenomenon is the anti-freezing mechanism of p-CY01_LM.

TABLE 3

Differential scanning calorimetry (DSC) analysis of p-CY01_LM solutions

| Condition | Freezing (° C.) | Thawing (° C.) | ΔH (J/g) |
|---|---|---|---|
| $^\alpha$G,$^\beta$D 1% | −14.2 ± 1.2 | −2.2 ± 0.5 | 212.0 ± 3.8 |
| $^\alpha$G,$^\beta$D 1% + p-CY01_LM 0.5% | −13.9 ± 2.2 | −6.1 ± 1.0 | 139.3 ± 6.7 |
| $^\alpha$G,$^\beta$D 1% + p-CY01_LM 2.5% | −32.1 ± 3.1 | −8.7 ± 0.6 | 52.81 ± 8.7 |

$^\alpha$G and $^\beta$D represent glycerol and DMSO, and all experiments were performed after dissolution in ADSOL. ± SD was obtained through three repeated experiments.

Example 8: Ice Formation Inhibition of
p-CY01_LM Solution

Through analysis of ice crystal growth inhibition during freezing, the anti-freezing ability of p-CY01_LM was analyzed.

Figure 14:
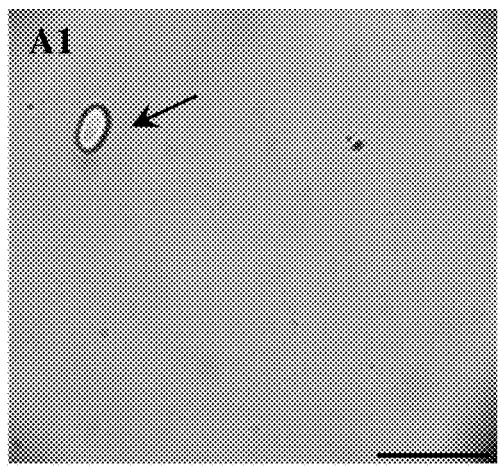
FIG. 14, panels A1 through C2, shows the results of analyzing the anti-freezing ability of p-CY01_LM solution by analysis of the ice crystal shape. Specifically, panels A1 and A2 show the results of analyzing the shape of ice crystals in a solution containing 1% glycerol and 1% DMSO; panels B1 and B2 show the results of analyzing the shape of ice crystals in an ADSOL solution (p-CY01_LM solution) solution containing 1% glycerol, 1% DMSO and 2.5% p-CY01_LM; and panels C1 and C2 show the results of analyzing the shape of ice crystals in an ADSOL solution containing 1% glycerol, DMSO and 2.5% HES. From 1 to 2 in each experimental group means that the shape of ice crystals becomes larger while ice crystal seeds are cooled. The scale represents 10 μm.
Figure 14:
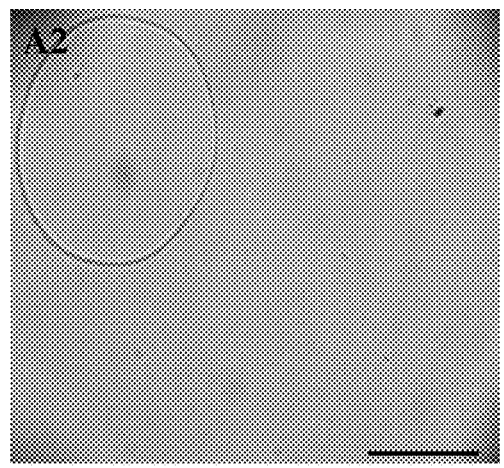
Figure 14:
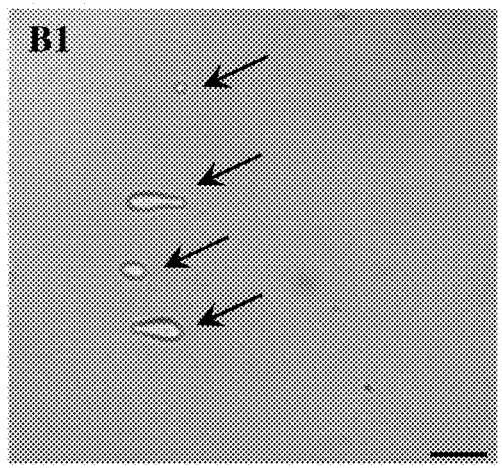
Figure 14:
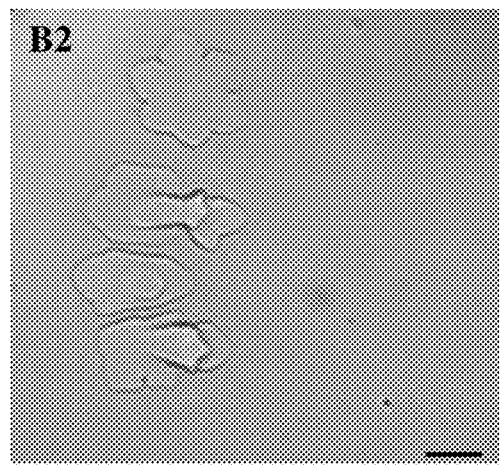
Figure 14:
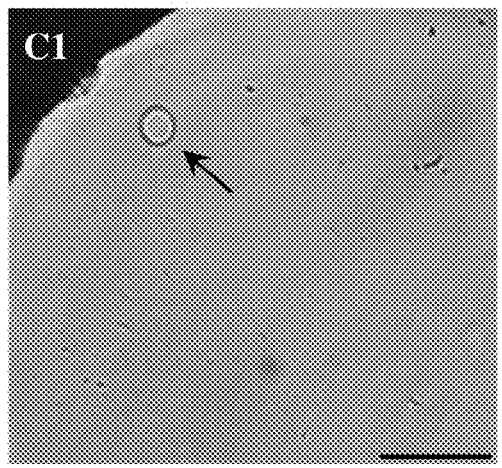
Figure 14:
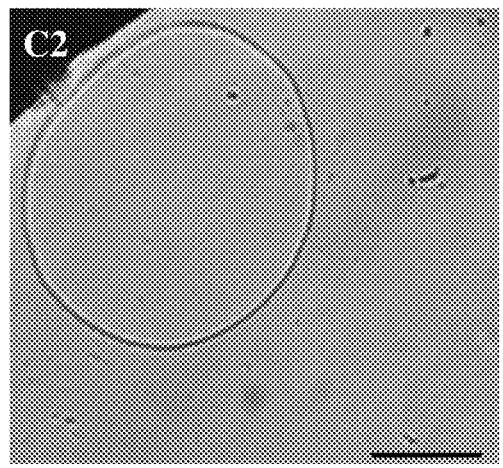

As shown in FIG. 14, panels A1 through C2, the growth of ice crystal seeds (FIG. 14, panel B1) in the p-CY01_LM solution (ADSOL containing 1% glycerol, DMSO and 2.5% p-CY01_LM) was inhibited with decreasing temperatures, and thus the ice crystal seeds grew in the form of six-pointed stars (FIG. 14, panel B2). This phenomenon frequently appears in anti-freezing proteins, and is the anti-freezing mechanism of p-CY01_LM. However, in the control (ADSOL containing 1% glycerol and DMSO) and the HES solution (ADSOL containing 1% glycerol, DMSO and 2.5% HES), the growth of ice crystal seeds was not inhibited, and thus the ice crystal seeds grew into circular or flat ice crystals (FIG. 14, panels A1 to A2 and panels C1 to C2), indicating that the anti-freezing effect by ice crystal growth inhibition was not observed. In addition, the super cooling point of the negative control water is −15.9° C., whereas the super cooling point of the p-CY01_LM solution is −30.5° C. as shown in Table 3 above. Such results indicate that p-CY01_LM has an anti-freezing effect.

Example 9: Real-Time Cryomicroscopic
Observation of Red Blood Cells During Freezing
and Thawing Using an ice recrystallization inhibition (IRI) assay, the size of ice crystals during thawing was analyzed. In the presence of an ice recrystallization inhibitor, the size of ice crystals that are recrystallized during thawing will not greatly grow. Thus, in this Example, red blood cells and ice crystals were imaged using a cryomicroscope during freezing and thawing of red blood cells. Specifically, red blood cells were cooled to −40° C. at a rate of 25° C./min in each of an ADSOL solution containing 2.5% p-CY01_LM and an ADSOL solution containing 2.5% (v/v) HES. The temperature of the samples was elevated to −6° C. at a rate of 25° C./min, and then the samples were photographed while they were allowed to stand for 5 minutes.

Figure 15:
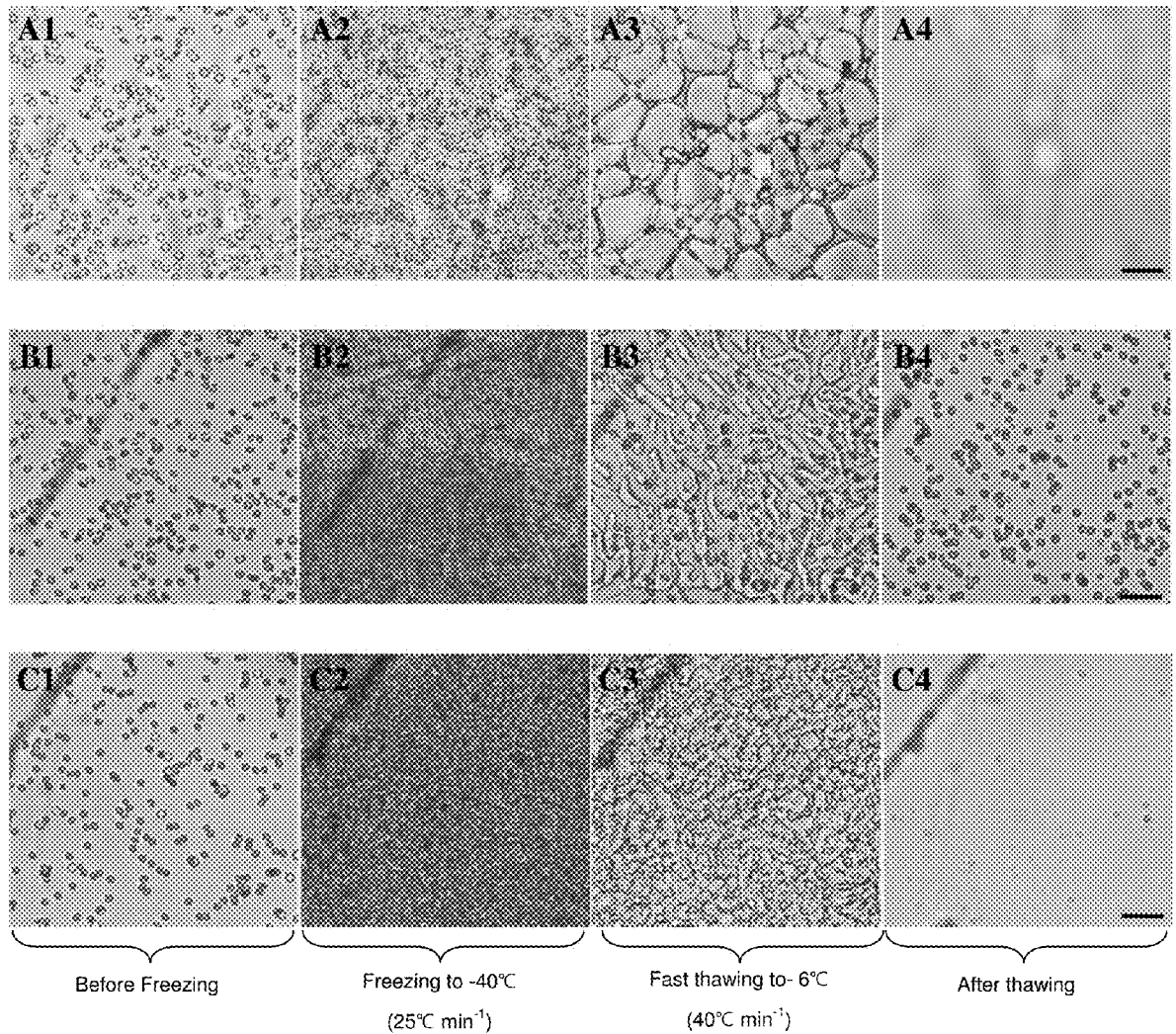
FIG. 15, panels A1 through C4, shows the results of analyzing the anti-freezing ability of p-CY01_LM by analyzing the remaining shape of red blood cells and the shape of ice crystals while microscopically observing freezing and thawing processes. Specifically, panels A1 through A4 show the shape of red blood cells in PBS; panels B1 through B4 show the shape of red blood cells in p-CY01_LM solution; and panels C1 through C4 show the shape of red blood cells in an ADSOL solution containing 1% glycerol, DMSO and 2.5% HES. Hemolytic images of red blood cells were obtained after 5 minutes in each step, and the scale represents 20 μm.

FIG. 15, panels A1 through C4, show images of red blood cells and ice crystals after recrystallization in the presence or absence of 2.5% p-CY01_LM. It was shown that, in the presence of 2.5% p-CY01_LM (FIG. 15, panels B1 to B2), the size of recrystallized ice crystals was significantly smaller than that in PBS (FIG. 15, panels A1 to A2) or the 2.5% HES-containing solution (FIG. 15, panels C1 to C2). Particularly, after red blood cells were completely thawed, it was observed that the shape of the red blood cells was maintained intact (FIG. 15, panels A4, B4 and C4).

Such results were confirmed again by measuring the IRI activity of p-CY01_LM. Specifically, polynuclear ice wafers having a diameter of less than 10 μm were grown at −6° C. for 30 minutes, and then the size of the ice crystals was compared with that of a control (PBS).

As shown in FIGS. 16A through 16C, the results of measurement for PBS (FIG. 16A), 2.5% (w/v) p-CY01_LM (FIG. 16B) and 2.5% (v/v) HES (FIG. 16C) indicated that the p-CY01_LM-containing solution showed distinct IRI activity at the same concentration, and thus inhibited ice recrystallization, but HES did not show a particular inhibitory effect on ice recrystallization.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

[Deposit of Microorganisms]
Depository Institution: Korea Research Institute of Bioscience and Biotechnology
Accession Number: KCTC 12867BP
Deposit Date: Jul. 15, 2015.
Address: 125 Gwahak-ro, Yuseong-gu, Daejeon 34141, Korea.
Strain: *Pseudoalteromonas* sp. strain CY01

The invention claimed is:

1. A composition for cryoprotecting at least one cell comprising:
    an exopolysaccharide with a molecular weight of $1.0 \times 10^5$ to $4.3 \times 10^5$ Da, which is obtained by acidolysis of the exopolysaccharide which is produced by *Pseudoalteromonas* sp. strain CY01 (KCTC 12867BP), wherein the molar ratio of the glucose and the galactose in the exopolysaccharide produced by *Pseudoalteromonas* sp. strain CY01 (KCTC 12867BP) and the exopolysaccharide obtained by acidolysis of that exopolysaccharide is 3.4:1; and
    the at least one cell,
    wherein the at least one cell is selected from the group consisting of fungi cells, animal cells, plant cells, red blood cells, platelets, spermatocytes, oocytes, cells constituting tissues, and cells constituting organs, and
    wherein the at least one cell is not *Pseudoalteromonas* sp. strain CY01 (KCTC 12867BP).

2. T composition of claim 1 further comprising dimethyl sulfoxide (DMSO).

* * * * *